United States Patent
Stevenson et al.

(10) Patent No.: US 7,012,192 B2
(45) Date of Patent: Mar. 14, 2006

(54) FEEDTHROUGH TERMINAL ASSEMBLY WITH LEAD WIRE BONDING PAD FOR HUMAN IMPLANT APPLICATIONS

(76) Inventors: Robert A. Stevenson, 15349 Iron Canyon Rd., Santa Clarita, CA (US) 91387; Richard L. Brendel, 1551 Jefferson Dr., Carson City, NV (US) 89706; Christine Frysz, 11908 Mekenie Ct., Marriottsville, MD (US) 21104; Haytham Hussein, 2140 Harrow Dr., Woodstock, MD (US) 21163; Scott Knappen, 1504 Winchester Rd., Annapolis, MD (US) 21401

( * ) Notice: Subject to any disclaimer, the term of this patent is extended or adjusted under 35 U.S.C. 154(b) by 0 days.

(21) Appl. No.: 11/096,003

(22) Filed: Mar. 30, 2005

(65) Prior Publication Data
US 2005/0247475 A1 Nov. 10, 2005

Related U.S. Application Data

(63) Continuation-in-part of application No. 10/842,967, filed on May 10, 2004.

(51) Int. Cl.
*H01L 23/02* (2006.01)
(52) U.S. Cl. ............ 174/52.5; 257/699; 257/708; 607/116
(58) Field of Classification Search .......... 174/52.1, 174/52.5; 257/698, 699, 708, 709
See application file for complete search history.

(56) References Cited

U.S. PATENT DOCUMENTS

| | | |
|---|---|---|
| 2,756,375 A | 7/1956 | Peck |
| 3,235,939 A | 2/1966 | Rodriguez et al. |
| 3,538,464 A | 11/1970 | Walsh |
| 3,920,888 A | 11/1975 | Barr |
| 4,083,022 A | 4/1978 | Nijman |
| 4,144,509 A | 3/1979 | Boutros |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,339,231 A * | 7/1982 | Conery et al. ............. 417/40 |
| 4,352,951 A | 10/1982 | Kyle |
| 4,362,792 A | 12/1982 | Bowsky et al. |
| 4,424,551 A | 1/1984 | Stevenson et al. |
| 4,456,786 A | 6/1984 | Kyle |
| 4,737,601 A | 4/1988 | Gartzke |
| 4,741,710 A | 5/1988 | Hogan et al. |
| 4,897,711 A * | 1/1990 | Blonder et al. ............ 257/48 |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,539,611 A | 7/1996 | Hegner et al. |
| 5,650,759 A | 7/1997 | Hittman et al. |

(Continued)

OTHER PUBLICATIONS

Dr. Gary Ewell, "A Capacitor's Inductance", Capacitor and Resistor Technology Symposium (CARTS-Europe), Lisbon, Portugal, Oct. 19-22, 1999.

*Primary Examiner*—Hung V. Ngo
(74) *Attorney, Agent, or Firm*—Kelly Lowry & Kelley, LLP

(57) ABSTRACT

A terminal assembly for active implantable medical devices includes a structural pad, in the form of a substrate or attached wire bond pad, for convenient attachment of wires from the circuitry inside the implantable medical device.

106 Claims, 23 Drawing Sheets

U.S. PATENT DOCUMENTS

| | | |
|---|---|---|
| 5,670,063 A | 9/1997 | Hegner et al. |
| 5,751,539 A | 5/1998 | Stevenson et al. |
| 5,759,197 A | 6/1998 | Sawchuk et al. |
| 5,825,608 A | 10/1998 | Duva et al. |
| 5,836,992 A | 11/1998 | Thompson et al. |
| 5,867,361 A | 2/1999 | Wolf et al. |
| 5,870,272 A | 2/1999 | Seifried et al. |
| 5,905,627 A | 5/1999 | Brendel et al. |
| 5,959,829 A | 9/1999 | Stevenson et al. |
| 5,973,906 A | 10/1999 | Stevenson et al. |
| 6,008,980 A | 12/1999 | Stevenson et al. |
| 6,031,710 A | 2/2000 | Wolf et al. |
| 6,034,424 A * | 3/2000 | Fujimura et al. ........... 257/696 |
| 6,414,835 B1 | 7/2002 | Wolf et al. |
| 6,459,931 B1 | 10/2002 | Hirschman |
| 6,459,935 B1 | 10/2002 | Piersma |
| 6,557,635 B1 | 5/2003 | Nguyen et al. |
| 6,844,023 B1 * | 1/2005 | Schulman et al. ......... 427/2.24 |

* cited by examiner

THERMOPLASTIC POLYIMIDE SUPPORTED TAPE ADHESIVE

| ABLELOC (R) 5500 MECHANICAL PROPERTIES | TEST METHOD |
|---|---|
| 90° Peel Strength - 250 mil (6.3 mm) width<br>Alloy 42 substrate @ 25°C: 5.0 lb$_f$ (2.3 kg$_r$) peak<br>@ 230°C: 1.4 lb$_f$ (0.64 kg$_r$) peak<br><br>PI Coated Si Substrate @ 25°C: 5.5 lb$_f$ (2.5 kg$_r$) peak<br>@ 230°C: 1.2 lb$_f$ (0.55 kg$_r$) peak | MT-8 |
| Flatwise Tensile Strength - 250 mil² (6.3 mm²)<br>Alloy 42 substrate @ 25°C: 3300 psi (93 kg)<br>@ 230°C: 450 psi (13 kg) | MT-1 |

(1) TH exposure - 16 hours, 85°C/85% RH

FIG. 3

FEEDTHROUGH TERMINAL ASSEMBLY WITH LEAD WIRE BONDING PAD FOR HUMAN IMPLANT APPLICATIONS

RELATED APPLICATION

This application is a continuation-in-part of U.S. application Ser. No. 10/842,967, filed May 10, 2004.

BACKGROUND OF THE INVENTION

This invention relates generally to terminal subassemblies and related methods of construction, particularly of the type used in active implantable medical devices such as cardiac pacemakers, implantable defibrillators, cochlear implants, neurostimulators, active drug pumps, and the like. More particularly, the present invention relates to an improved terminal assembly that includes bonding pads for convenient attachment of a lead wire by way of thermal or ultrasonic bonding, soldering or the like.

Feedthrough terminal assemblies are generally well known for connecting electrical signals through the housing or case of an electronic instrument. For example, in implantable medical devices, the terminal pin assembly comprises one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. In a cardiac pacemaker, for example, the feedthrough terminal pins are typically connected to one or more lead wires within the case to conduct pacing pulses to cardiac tissue and/or detect or sense cardiac rhythms.

SUMMARY OF THE INVENTION

Feedthrough terminal assemblies constructed in accordance with the present invention comprise, generally, a conductive ferrule conductively coupled to a housing of the active implantable medical device. A conductive terminal pin extends through the ferrule in non-conductive relation. An insulator is disposed between the terminal pin and the ferrule. A structural pad, in the form of a substrate and/or a wire bond pad, is disposed adjacent to the insulator and conductively couples a lead wire to the terminal pin.

The co-bonded circuit board or substrate contains via holes, circuit traces and bonding pads or bonding areas such that it is convenient to attach wires from the circuitry inside the implantable medical device via thermosonic bonding, ultrasonic bonding, thermal-setting conductive adhesives, soldering, welding, brazing, mechanical attachments or the like. In a preferred embodiment, a novel circuit board or substrate is co-bonded to the top surface of the insulator in accordance with the invention. The co-bonding is performed with a thin layer of high temperature thermal-setting material such as a nonconductive polyimide. Ideal material for this application is a thermal plastic polyimide supported tape adhesive whose properties are described herein in FIG. 3. There are a number of alternate materials that can be used to co-bond the circuit board or substrate to the surface of the insulator including various nonconductive thermal-setting polymers such as high temperature thermal-setting epoxies, silicones, polyimides, adhesives, sealants and the like. Another method of co-bonding could include co-firing with low temperature glasses, ceramics or the like.

The substrate or circuit board can be made of a number of materials that are common in the art. For the present application, an ideal ceramic substrate material would include, but are not limited to the group of: Aluminum-oxide, Fosterite, Alumina in various purities, Berrylia and Aluminum Nitride. These ceramic substrates are well known in the art, have good mechanical or laser scribe characteristics. For ceramic substrates, the scribe characteristics of the ceramic material is important so that the individual substrates of the present invention can be cut or snapped out of the larger production array of such substrates.

Non-ceramic printed circuit board materials can also be used as a circuit board substitute for the ceramic substrate of the present invention and are mostly constructed from a resin reinforced by a fabric cloth. Epoxy (FR-4), polyimide and cyanate ester are the more common resin systems in use today. Fiberglass is the most popular fabric.

It is important that the circuit board substrate be able to withstand the high temperatures caused by laser welding of the hermetic terminal assembly with wire bonds into the housing of an implantable medical device. Non-ceramic circuit board temperature range is most often expressed as the glass transition temperature (Tg) of the material. The material's Tg is the point above which the mechanical properties of the material begin to rapidly deteriorate. Printed circuit board materials change from hard, brittle substances to soft, rubber like substances after they reach their glass transition temperature. Typical Tg ratings for the more common material systems are as follows:

|  | Tg |
|---|---|
| Polyimides | 260° C.–270° C. |
| Modified Polyimides | 240° C.–260° C. |
| Cyanate Esters | 240° C.–250° C. |
| BT* Epoxies | 225° C.–240° C. |
| Composite Epoxies | 240° C.–260° C. |
| MultiFunctional Epoxies | 160° C.–190° C. |
| TetraFunctional Epoxies | 140° C.–160° C. |
| Modified FR*-4's | 120° C.–130° C. |
| Standard FR*-4's | 115° C.–125° C. |

*BT = Barium Titanate FR = fiber reinforced

Accordingly, one can see from the above listing, that polyimides, followed by cyanate esters and BT epoxies would be a preferred choice after ceramic substrates as an alternative for the present invention. As used herein, the word substrate or alumina substrate can include any of the ceramic or non-ceramic materials listed above, in addition to many others that are not shown. It is desirable that the material that bonds the substrate of the circuit board to the ceramic capacitor be somewhat flexible and stress absorbing. Accordingly, polyimide is an ideal material in that it forms a ring type of molecule after it goes through its glass transition temperature of approximately 2600° C. Compared to epoxy, this material tends to absorb stresses and is quite resilient.

It is desirable that the circuit board or substrate be relatively thin. This means that materials having a high structural integrity must be used. This is another reason that the use of alumina, aluminum oxide, Fosterite, or polyimide as a substrate material is ideal. The construction of such substrates with circuit trace wire bond pads is well known in the art. Photo-resist, chemical etching, automated screen printing, silk screening, selective plating, screen printing and thin or thick film deposition methods are typically used to lay down the conductive circuit trace patterns, the bond pads or "lands" and the location and metallization of via holes. Typical screen printing formulations are generally well known in the art and include, but are not limited to:

Screen Printing Ink Formulations

The ink consists of four distinct groups of intermediates, which are thoroughly mixed and blended, yielding a homogeneous product:

| | |
|---|---|
| Functional Phase | Consists of metal powders (Pt, Pd, Ag, Au, etc.) in conductive inks, metals and/or metal oxides ($RuO_2$, $Bi_2 Ru_2O_7$, Pd, Ag) in resistors and ceramic/glass ($BaTiO_3$, glass) in dielectric temperature firing. |
| Binder Phase | To hold the ink to the ceramic substrate, and merges with the ceramic during high temperature firing. |
| Vehicle | Acts as the carrier for the powders and is composed of both volatile (solvents) and non-volatile (polymers) organics. These evaporate and burn off during the early stages of drying and firing, respectively. |
| Modifiers | Are small amounts of proprietary additives which control behavior of the inks before and after processing. |

1. Conductor Pastes - Single metal systems (such as, Pd, Ag, Au, Ni, etc.)
2. Conductor Pastes - Binary metal systems (such as, Ag/Pd, Ag/Pt, etc), Tungsten (W), Tungsten/Nickel and equivalent.
3. Conductor Pastes - Ternary metal systems (such as, 40Au/40Pd/20Pt, 60Ag/20Pt/20Pd, 35Ag/25Pd/20Au/20Pt, etc.)
4. High fire systems (such as, 30Ag/70Pd with $BaTiO_3$ or ZrO additives, 100Pd, etc.)
5. Base metal systems (such as, Ni with $BaTiO_3$ or ZrO additives, etc.)

Substrate via holes are typically formed by automated pattern recognition drilling machines. There are a number of methods of providing metallization on the circuit paths, the bonding pads and through the via holes, including screen printing selective plating, metallization vacuum pull through, screen printing, cladding followed by selective etching, physical vapor deposition (PVD), chemical vapor deposition (CVD), and the like. Since these techniques are well known in the art, they will not be completely described herein. In a preferred embodiment of the invention, it is desired to form one or more wire bond pads suitable for thermal or ultrasonic bonding. In such applications, a gold or gold plated bond pad is desirable. In the preferred embodiment, the bond pad is plated of ultrapure soft gold, such as 99.99% purity. Such gold is also known as yellow gold, is quite soft and to which forming a wire bond is easy. In a typical application, the wire bond pad is laid down directly on the substrate or it can be a Kovar or Alloy 42 attached metal pad with a nickel under-plate and then finished with a soft gold over-plate. Chemical or photo-resist techniques, electroplating, electroless plating and the like can be used to prevent deposition of plating, such as the gold, in the wrong places. The bond pad itself is typically Kovar or Alloy 42 but can include many other metals, ceramics and other materials.

Kovar or other metal wire bond pads are preferably attached to the outside or perimeter of a bonded substrate. Another embodiment is to add Kovar wire bond pads surrounding the feedthrough terminal pin where a convenient and highly reliable laser weld can be made. Another inventive concept is the addition of a multi-layer substrate with embedded circuit paths. For higher current applications, one or more embedded circuit paths can be added in parallel. In the cross-section of such multi-layer pads the internal circuits can be different on different planes.

It should be noted that if lead-attachment is made by soldering or the like, the Kovar or Alloy 42 pad is generally not required. However, during ultrasonic or thermal wire bonding, considerable energy is imparted into the structure. Accordingly, in this case, a Kovar pad is desired to dissipate energy away from the underlying ceramic substrate. Various substrates are well known in the art with wire bond pads and are typically used in combination with hybrid circuit electrical connections and the like.

For implantable medical devices, it is generally required that any of the electrical circuit connections that are in series with the input or output of the device should be of highly reliable connections. For example, in a cardiac pacemaker, the lead wires that are implanted in the heart sense both biologic electrical signals and also provide pacing pulses to correct cardiac arrhythmias. It is generally not acceptable to have an opening or break in this lead wire anywhere in the system that would then be reattached during initial manufacturing with solder, conductive thermal-setting adhesives or the like. Accordingly, it is a desirable feature of the present invention to have a laser welded connection between a Kovar or Alloy 42 pad and the hermetic terminal lead wire, and/or a gold, gold alloy or CuSil (copper-silver alloy) braze between the Kovar pads and the perimeter or outside diameter of the substrate. The connection from the wire bond pad is generally accomplished by ultrasonic or thermosonic bonding of a pure gold wire directly to the pure gold plating of the pad. Attachment of lead wire(s) to wire bond pads can also be accomplished by soldering, conductive polymers, welding, brazing or a variety of mechanical attachment methods including machine screws and the like. In a typical pacemaker application, this pure gold wire is approximately 0.005 inch in diameter and would terminate on a similar wire bond pad on the pacemaker hybrid circuit substrate or circuit board on which microprocessor wire bonding and other implantable medical device electronics are mounted. Automated wire bonding equipment is readily available and well known in the art.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is a table specifying the properties of a thermal plastic polyimide supported tape adhesive;

DETAILED DESCRIPTION OF THE PREFERRED EMBODIMENTS

Reference will now be made in detail to presently preferred embodiments of the invention, examples of which are represented in the accompanying drawings for purposes of illustration. Such examples are provided by way of an explanation of the invention, not a limitation thereof. In fact, it will be apparent to those skilled in the art that various modifications and variations can be made in the present invention, without departing from the spirit and scope thereof. For instance, figures illustrated or described as part of one embodiment can be used on another embodiment to yield a still further embodiment. Still further, variations and selection of materials and/or characteristics may be practiced, to satisfy particular desired user criteria. Thus, it is intended that the present invention cover such modifications and variations as come within the scope of the present features and their equivalents. In the following description, functionally equivalent components of the various embodiments will be assigned the same reference number, or, if similarly related, a similar reference number increased by 100, for example, for sake of clarity and ease of explanation.

Figure 1:
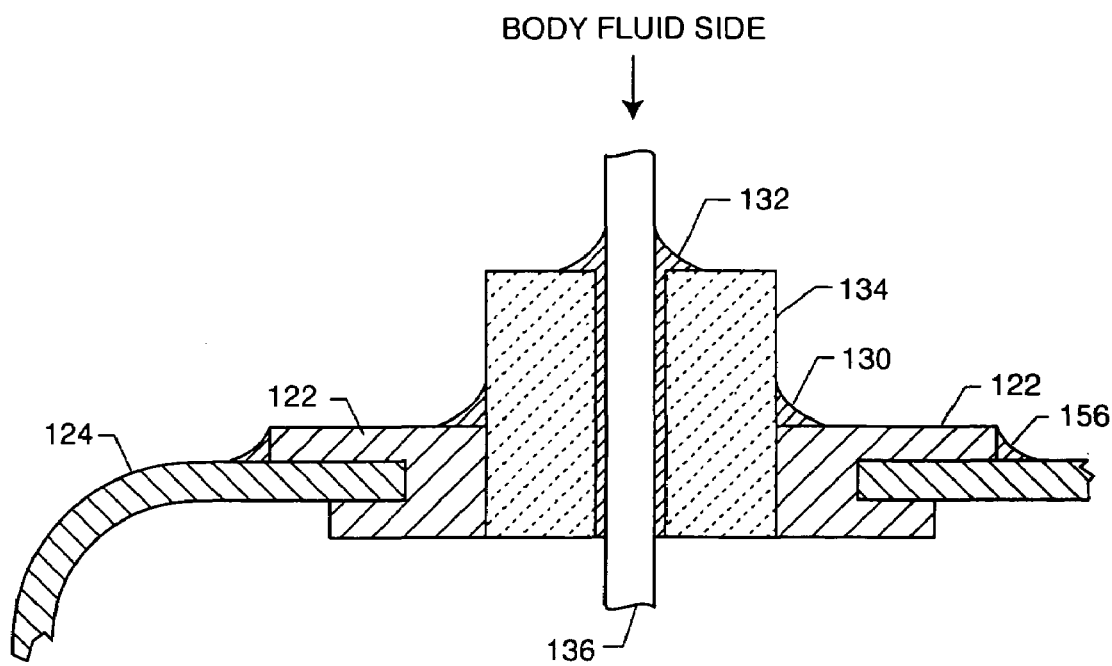
FIG. 1 is a prior art fragmented cross-sectional view of a prior art feedthrough terminal assembly comprising a hermetically sealed ferrule.

FIG. 1 is a cross-section drawing which illustrates a prior art feedthrough terminal assembly installed to the hermetically sealed ferrule 122 of a housing 124 of an implantable medical device. The connection between the housing 124 and the ferrule 122 is accomplished with a thermal-setting conductive adhesive 156. The hermetic terminal of FIG. 1 is formed by gold brazes 130 and 132. Braze 130 makes a 360 degree mechanical and hermetic seal between the ferrule 122 and the alumina ceramic insulator 134. Gold braze 132 forms a 360 degree mechanical and hermetic seal between the terminal pin 136 and the alumina ceramic terminal 134.

Figure 2:
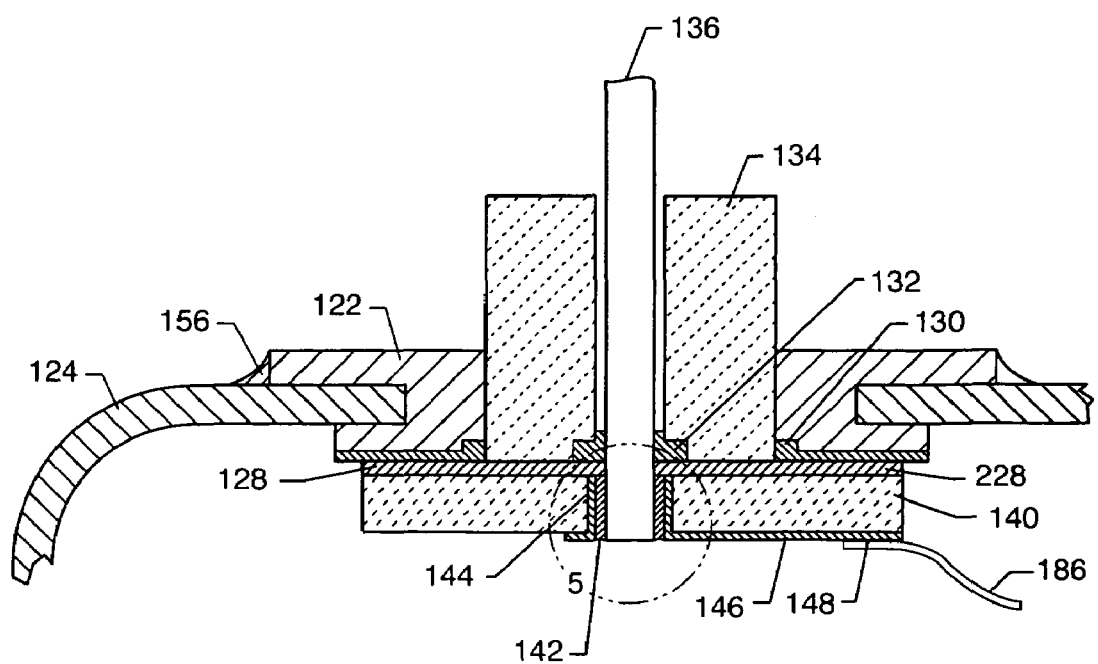
FIG. 2 is a sectional view illustrating a circuit board or substrate of the present invention co-bonded to a feedthrough terminal assembly and a lead wire extending therefrom.

FIG. 2 is the feedthrough terminal assembly of FIG. 1 with a circuit board or substrate 140 co-bonded to the insulator 134. The substrate 140, in a particularly preferred embodiment, is a thin alumina or aluminum oxide ceramic or equivalent insulative disk. A thin layer of nonconductive polyimide 228 bonds the alumina substrate 140 to the insulator 134. In the preferred embodiment, a conductive thermal-setting polymer, solder or braze joint 142 electrically connects the inside diameter metallization 144 of the via hole through the ceramic substrate 140 to the terminal pin 136. In turn, this also connects terminal pin 136 by way of the via hole metallization 144 to a continuous circuit trace 146 to the wire bond pad area 148 which is more readily seen in FIG. 4. The wire bond pad area 148 generally consists of a pure gold layer which is thick enough for conventional wire bonding. A lead wire 186 is shown attached to bond pad area 148 by thermosonic or ultrasonic wire bonding. Lead wire 186 can then be routed to Active Implantable Medical Device (AIMD) internal circuits (not shown).

It should be pointed out that in human implant applications, the purpose of the hermetic terminal is to allow conductive terminal pin 136 to pass in nonconductive relationship through the titanium housing or can 124 of the pacemaker, neurostimulator, or implantable cardioverter defibrillator. Accordingly, all materials used on the body fluid side of such can or housing must be biocompatible. This limits the materials that can be used to noble metals, titanium, stainless steel and the like. Usually the terminal pin 136 shown in FIG. 2 would be of platinum, platinum-iridium alloy, tantalum, niobium or the like. If the terminal pin 136 is platinum or platinum-iridium, these are highly solderable materials and therefore, it is easy to form a well wetted solder joint or conductive polymer connection between the inside diameter metallization 144 of the alumina substrate 140 and the outside diameter of the terminal pin 136. However, if the lead wire is constructed of tantalum or niobium, these materials are generally not easily wetted by solder or conductive polymers. This can complicate the solder or conductive polymer joint 142 shown in FIG. 2 and its exploded view in FIG. 5. This is because niobium and tantalum form a heavy oxide layer on their surfaces. Accordingly, a niobium or tantalum terminal pin 136 must be pretreated so that a solder joint or connection 142 with a conductive thermal-setting material can be accomplished. It is a feature of the present invention to pretreat such leads such that they can be reliably electrically connected to via hole metallization 144 of the substrate 140. U.S. Pat. No. 6,159,560 describes a method of depositing silver on a tantalum pin to displace surface oxide and deposit a conductive finish suitable for making an electrical connection. There are other pin metal coating methodologies, including sputter or vacuum deposition (as described in U.S. Pat. No. 5,531,003), of materials such as gold, titanium and other conductors which can then be followed up with surface plating with gold, iridium or the like.

FIG. 3 is a Table which specifies the properties of a thermal plastic polyimide supported tape adhesive 228 which is ideal for laminating the substrates 140 of the present invention to the insulator 134 surface. The industry designation for this is ABLELOC(R)5500. This material is convenient in that it can be die cut, stamped or laser cut into convenient geometries to co-bond an alumina substrate 140 to the hermetic terminal 122 or insulator 134. In addition, polyimide is an ideal high-temperature material that will readily withstand the installation stresses into the implantable medical device caused by laser welding. A number of other bonding materials can also be used including liquid polyimides, adhesives, epoxies, glasses and the like.

Referring now back to FIG. 2, the cross-sectional view of the alumina substrate 140 illustrates a top circuit trace metallization layer 146. Metallization 146 is continuous from the inside diameter via hole of the substrate 144 all the way over to the wire bond pad area which is shown in cross-section FIG. 2 as 148.

Figure 4:
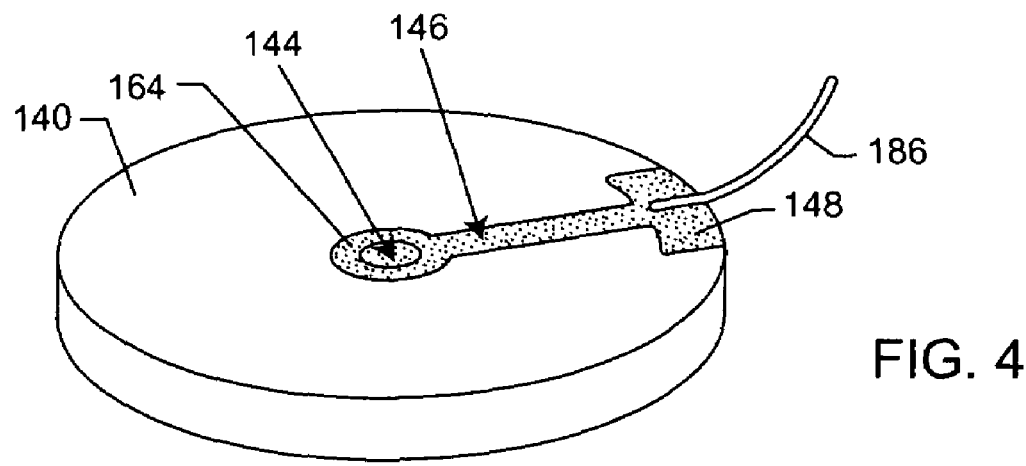
FIG. 4 is a perspective view of the circuit board or substrate and lead wire illustrated in FIG. 2.

FIG. 4 better illustrates the circuit board or substrate 140 as previously described in FIG. 2. It should be noted that in FIG. 4 the circuit board or substrate 140 is shown inverted so that the wire bond area 148 and circuit trace(s) 146 can be readily observed. The circuit trace 146 is conductive and metallic in nature. The wire bond pad area 148, in the preferred embodiment, is finished with high purity gold suitable for thermal or ultrasonic bonding of a gold lead wire to the circuitry inside the implantable medical device. In the preferred embodiment, the substrate 140 is made of a solid highly insulative material like ceramics such as alumina, aluminum oxide or Fosterite. This solid insulative substrate 140 is then co-bonded to the insulator 134 as previously described in FIG. 2 using a thermal plastic polyimide supportive tape adhesive 228 such as described in FIG. 3 and shown in FIG. 2.

Referring now again to FIG. 2, the plated or metallized through via hole 144 is shown installed over terminal pin 136. It is important to note that the electrical connection using material 142 between the feedthrough terminal pin 136 and the inside diameter metallization 144 of the circuit board or substrate is very important. The electrical connection material 142, such as solder, conductive polyimide, conductive epoxy or the like, desirably penetrates into the angular space between the inside diameter of the metallized hole 144 of the substrate 140 and the outside diameter of the terminal pin 136. This puts the electrical connection material 142 in shear as opposed to having just an electrical connection on top. This is very important to make a highly reliable electrical connection.

A significant deficiency in previous designs, such as U.S. Pat. Nos. 6,031,710 and 5,870,272 and 5,867,361, is that the series connection between the terminal pin 136 and the wire bond pad 140 depends on a large mass of solder in series. This is not an optimal situation. It has been known in U.S. Space programs for a number of years that a designer should not rely on solder, conductive epoxies or the like in a large mass which could later result in an open circuit during use. For lead wire connections, it is generally a NASA policy to have a mechanical connection before a solder joint is formed. This is particularly important in a spacecraft application where such electrical connections are subjected to high shock and vibration forces. However, a similar situation occurs during ultrasonic wire bonding. By nature of the ultrasonic bonding process, significant vibration forces are set up on the wire bond pad which can transmit to the electrical connection material 142. Accordingly, as seen in FIG. 2, a highly reliable "in shear" electrical connection using material 142 is made between the inside diameter metallization 144 of the circuit board or substrate 140 and the terminal pin 136.

Figure 5:
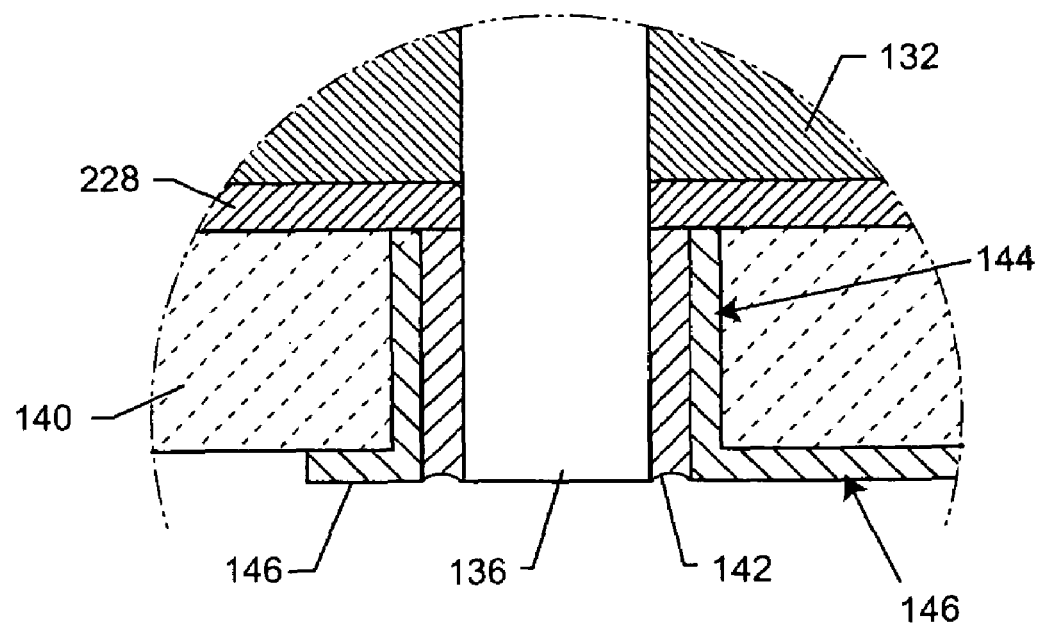
FIG. 5 is an enlarged view of the structure of area "5" of FIG. 2.

As mentioned, FIG. 5 is an enlarged cross-section view of FIG. 2 showing the detail of the electrical connection between terminal pin 136 and the via hole metallization 144 of substrate 140 more clearly. In a previous operation, this ceramic substrate 140 has been selectively metallized so that its through hole or via has conductive termination or plating 144 on the inside diameter. There is a continuous metallic electrical connection 146 between the inside diameter metallization of the via hole 144 all the way over to the bond pad area 148 (which is not visible in FIG. 5). An important point is that the electrical connection material 142 is in shear between the terminal pin 136 and the inside diameter metallization 144 of substrate 140. Material 142 is of the group of solder, thermal-setting conductive adhesives, such as a thermal-setting conductive polyimide, braze or the like. As can be seen in FIG. 5, the electrical connection material 142 forms a 360 degree electrical connection joint around the terminal pin 136 and a 360 degree joint around the metallized inside diameter 144 of the substrate 140. This forms a highly reliable electrical connection in that material 142 has a large welted surface area that is in shear. In addition, the relative volumes of materials are such that the solder or conductive thermal-setting adhesive is used properly. In a very large mass, high tensile stresses can develop as solder, brazes or conductive adhesives shrink or when their thermal coefficients of expansion are mismatched with the surrounding materials. If solder is used to make the electrical connection 142 in FIG. 5, then it would be desirable if the solder is malleable, such as a high lead content solder. A preferred alloy would be alloy SN10, which is a common Kester solder. In addition, the metallized circuit trace 146 as seen in FIG. 4 forms a continuous metallized surface from the inside diameter metallization 144 of the via hole all the way to the wire bond pad area 148. Accordingly, the electrical connection from wire bond pad 148 through the circuit trace 146 to the inside diameter of the via hole 144 is continuous, conductive and highly reliable.

Referring now back to FIG. 4, the wire bond pad area 148 is not an ideal surface for attachment of a lead wire 186 by conventional thermosonic or ultrasonic wire bonding processes. It is preferred that a metallic wire bond pad made of Kovar, Alloy 42 or similar materials be used, as will be more fully described herein. It is well known in the art that these Kovar pads are usually nickel plated and then over-plated with an ultra-pure soft gold. The thermal or ultrasonic bonding of a pure gold lead wire is facilitated by the mating together of the two gold surfaces.

Wire bond attach area 148 need not be gold plated if the subsequent lead wire connection is to be made by soldering, welding, brazing or the like. In this case, the wire attach area could be tin, electro-tin plating, solder coat and the like.

Figure 6:
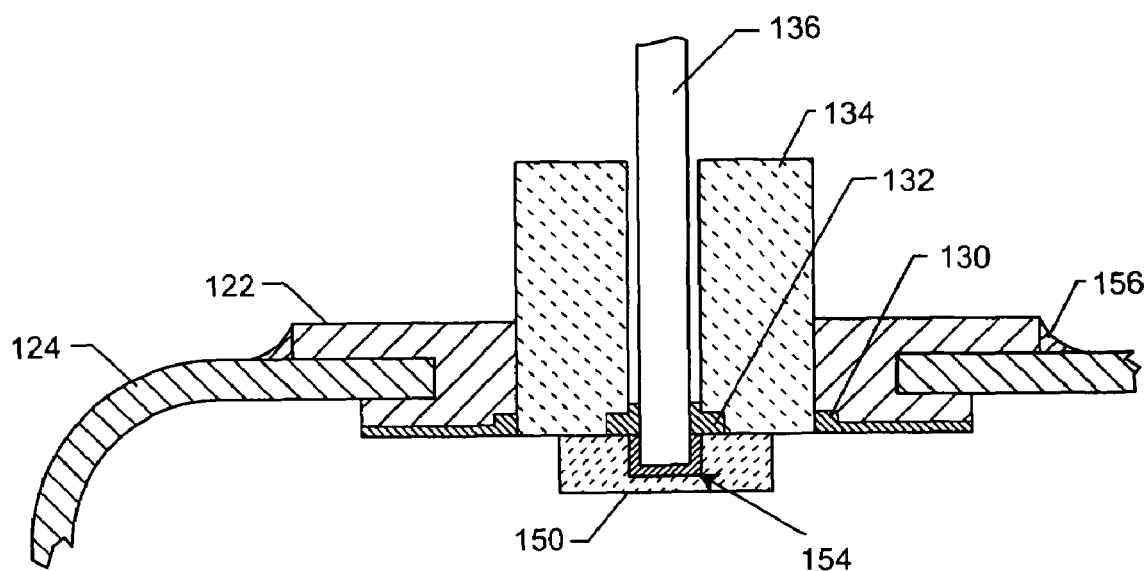
FIG. 6 is a sectional view illustrating use of a wire bond pad bonded or laminated onto a shortened terminal pin.

A novel method of providing a wire bond pad 150 is shown in FIG. 6. In this case, a counterbored Kovar or Alloy 42 disk 150, as also shown in FIGS. 7 and 8, is bonded or laminated over the terminal pin 136 by soldering, conductive thermal-setting adhesives, resistance welding, laser welding material 154 or the like.

Figure 7:
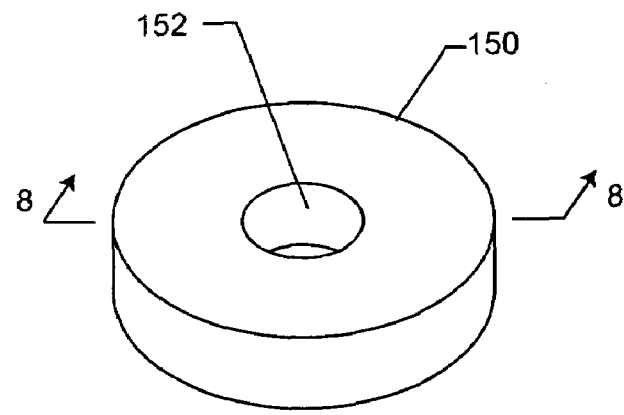
FIG. 7 is an enlarged perspective view of the wire bond pad of FIG. 6.
Figure 8:
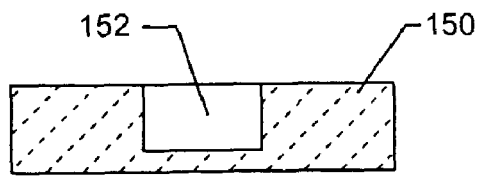
FIG. 8 is a sectional view taken generally along the line 8—8 of FIG. 7.

FIG. 7 is an isometric view of the wire bond cap 150 and FIG. 8 is a cross-sectional view of the wire bond cap 150 of FIG. 6. In the preferred embodiment, such wire bond cap 150 as shown in FIGS. 6 and 7 would be constructed of Kovar or Alloy 42. The Kovar would be nickel plated and then over plated with soft gold suitable for compatibility with ultrasonic, thermal or thermal sonic wire bonding processes. As discussed in the FIGS. 2 and 5 drawing descriptions, electrical connection material 154 is preferably placed in shear between the wire bond pad 150 and the terminal pin 136. Again, this is essential to form a highly reliable electrical connection that will withstand the vibration and shock forces associated with subsequent ultrasonic wire bond attachment(s). This shear area is accomplished by the counterbore area 152 shown in FIGS. 7 and 8. The wire bond cap 150 of FIG. 7 is also described in pending U.S. patent application Ser. Nos. 10/377,018, 10/377,272 and 10/377,086. FIGS. 44, 45, 46, 47A, 47B, 47C, 48 and 49 from pending U.S. patent application Ser. No. 10/377,086, entitled, EMI FEEDTHROUGH TERMINAL ASSEMBLY FOR HUMAN IMPLANT APPLICATIONS UTILIZING OXIDE RESISTANT BIOSTABLE CONDUCTIVE PADS FOR RELIABLE ELECTRICAL ATTACHMENTS, describes alternate methods to build the wire bond cap 150 shown in FIGS. 7 and 8.

In FIG. 6, an alternative method of forming the electrical connection 154 between the counterbore 152 of wire bond cap 150 and terminal pin 136 is by prior art resistance welding techniques. In resistance welding, the counterbore 152 of wire bond cap 150 would fit very tightly onto terminal pin 136. Electrical contacts would be placed on the outside diameter of wire bond cap 150 and a current pulse from the resistance weld machine would be applied sufficient to cause heating and reflow of metals and/or the plating of wire bond cap 150 to form a low resistance metallurgical bond to terminal pin 136.

Referring now back to FIG. 6, as illustrated, electrical connection material 154 also makes a reliable and oxide free electrical connection to the gold braze area 132. This important feature is described by co-pending U.S. patent application Ser. No. 10/377,086. The gold braze material 132 penetrates through any surface oxidation on terminal pin 136, for example, if terminal pin 136 is niobium or tantalum, and thereby forms a highly conductive and reliable hermetic seal connection. In turn, electrical connection material 154 also makes an electrical connection to the inside gold plated counterbore area 152 of the Kovar wire bond cap 150. This means that terminal pin 136 can be of any biocompatible material including oxidized materials such as niobium, and that no pretreatment, for example, sputter coating, is required to make a reliable electrical connection from terminal pin 136 to the gold plated wire bond cap 150. In other words, no direct electrical contact from the wire bond cap 150 is required to the terminal pin 136.

Figure 9:
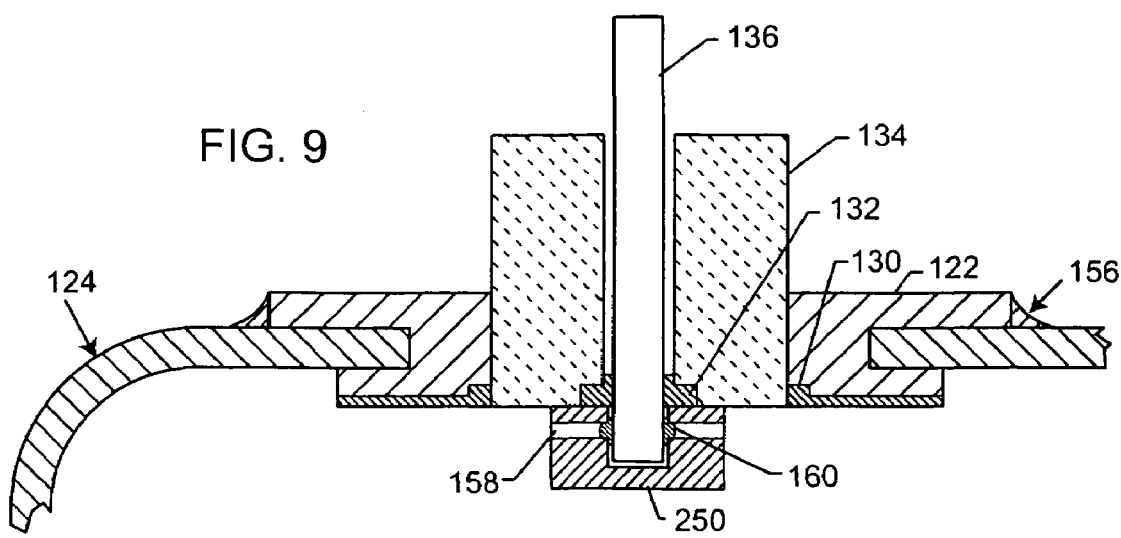
FIG. 9 is a sectional view similar to FIG. 6 illustrating another embodiment of the invention.

FIG. 9 illustrates another embodiment of the present invention. As previously mentioned, it is highly desirable in the output and input circuitry of implantable medical devices, that all electrical connections that are in series with the input and output be of highly reliable metallurgical joints. In other words, it is generally unacceptable to have a conductive thermal-selting polymer, conductive polyimide, or less reliable metallurgical joint such as solder to rely on in series with the terminal pins 136 that are connected, for example, to the human heart. Mechanically robust and reliable metallurgical joints are preferred and are generally of the group of laser welding, brazing and the like. A preferred embodiment illustrated in FIG. 9, overcomes such deficiencies with a wire bond pad 250 that has been modified to accommodate laser beam welding. Another advantage of using this laser weld approach is that lower cost hermetically sealed feedthrough terminals can be used. Lower cost means that the terminal pins 136 can be of niobium or tantalum construction instead of relatively expensive platinum or platinum-iridium alloys. Niobium and tantalum are notorious for forming heavy oxides on their surface and generally do not readily accept solder or thermal-setting conductive adhesives. Previous methods of making the electrical contact with niobium or tantalum terminal pins 136 include an expensive process of pre-treating the niobium with vacuum or sputter deposition processes or other metallic overcoating. Such overcoat materials can be platinum, gold and the like.

FIG. 9 overcomes all of these previous deficiencies with the novel assembly method as illustrated. FIG. 9 is similar to the unipolar hermetic terminal assembly of FIG. 2 with a metallic ferrule 122. The ferrule 122 is designed to be laser welded 156 into the housing 124 of an implantable medical device such as a cardiac pacemaker or implantable cardioverter defibrillator (ICD). Gold braze 130 forms a hermetic seal connection between the ferrule 122 and the alumina insulator 134. Gold braze material 132 makes the hermetic connection between the terminal pins 136 and the hermetic alumina insulator 134. It will be obvious to one skilled in the art that the alumina insulator 134 could be replaced by a variety of glasses or other sealing materials. It is a novel aspect of the wire bond cap 250 that it have one or more side through holes 158. These holes 158 are designed so that a laser beam from a laser welder can be directed into the through hole 158 to impinge its energy upon the terminal pin 136. Accordingly, a highly reliable laser weld connection 160 is formed between the counterbored wire bond cap 250 and the terminal pin 136.

The wire bond cap 250 can also be bonded or previously gold brazed 132 or 168 to the insulator 134 as shown. The laser weld 160 is then made by projecting a laser beam through the holes 158 in the wire bond cap 250.

Figure 10:
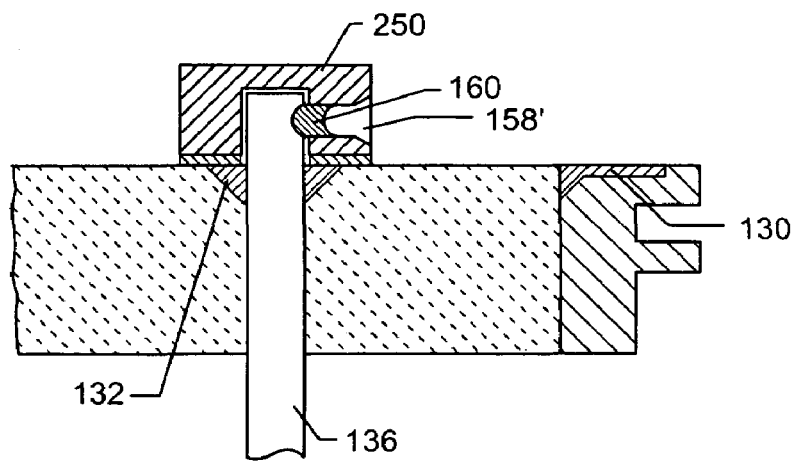
FIG. 10 is a partially fragmented sectional view illustrating use of an alternative wire bond pad.

As shown in FIG. 9, this laser weld 160 can be performed from one or more sides, achieving a very mechanically strong and low electrical resistivity connection 160. An alternative method is shown in cross-sectional view 10. One can see that the wire bond pad 250 has had its laser through hole 158' enlarged at the opening point. This can be done by a counter sink, counterbore or the like. In this way, it is easier to direct the laser beam energy against the terminal pin 136 thereby facilitating formation of the laser weld connection 160 between the wire bond cap 250 and the terminal pin 136. This can be done on one or more sides around the circumference of the wire bond cap 250. As stated, the laser weld hole 158', shown in FIG. 10, has a counterbore which enlarges the opening for the laser beam. This enlarged opening also facilitates easier fixturing and robot programming to form the laser weld 160 between the wire bond cap 250 and the terminal pin 136. In this particular embodiment, the terminal pin 136 can be of a non-wettable material such as niobium or tantalum.

Figure 11:
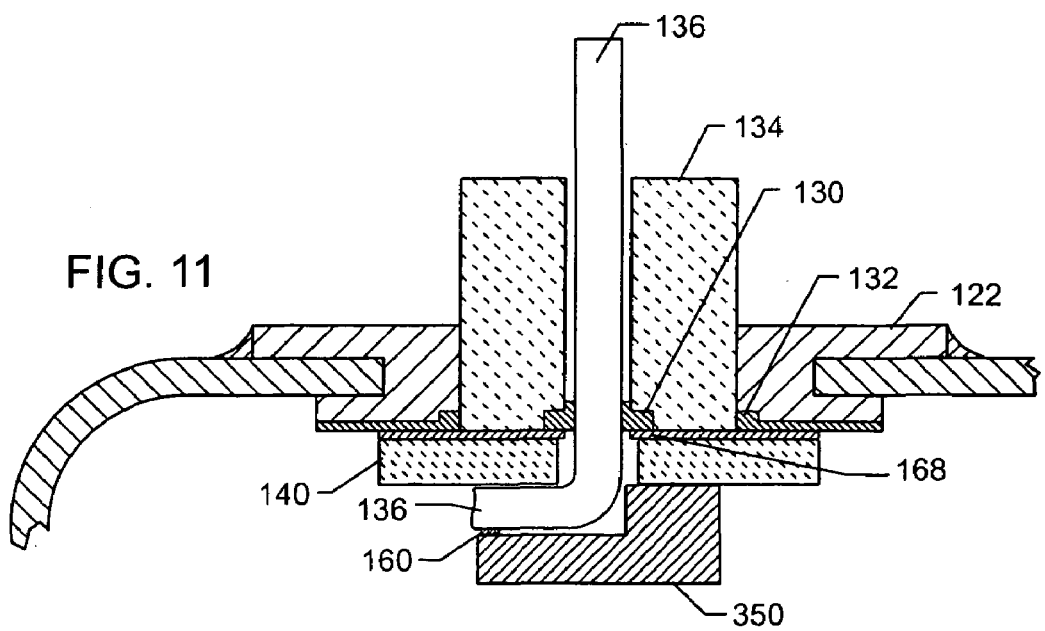
FIG. 11 is a fragmented cross-sectional view similar to FIG. 9, illustrating yet another alternative wire bond pad.

FIG. 11 is the hermetic terminal assembly of FIG. 9 with the wire bond pad 350 modified as shown. Terminal pin 136 is bent over at a 90 degree angle as shown in FIG. 11 thereby allowing the wire bond cap 350 to be welded 160 or bonded to the terminal pin 136 using a thermal-setting conductive adhesive, gold braze or solder. As previously mentioned, wire bond cap 350 would normally be made of Kovar or Alloy 42 and be first nickel plated and then over plated with a final finish an ultra-pure or soft gold suitable for wire bonding.

Figure 12:
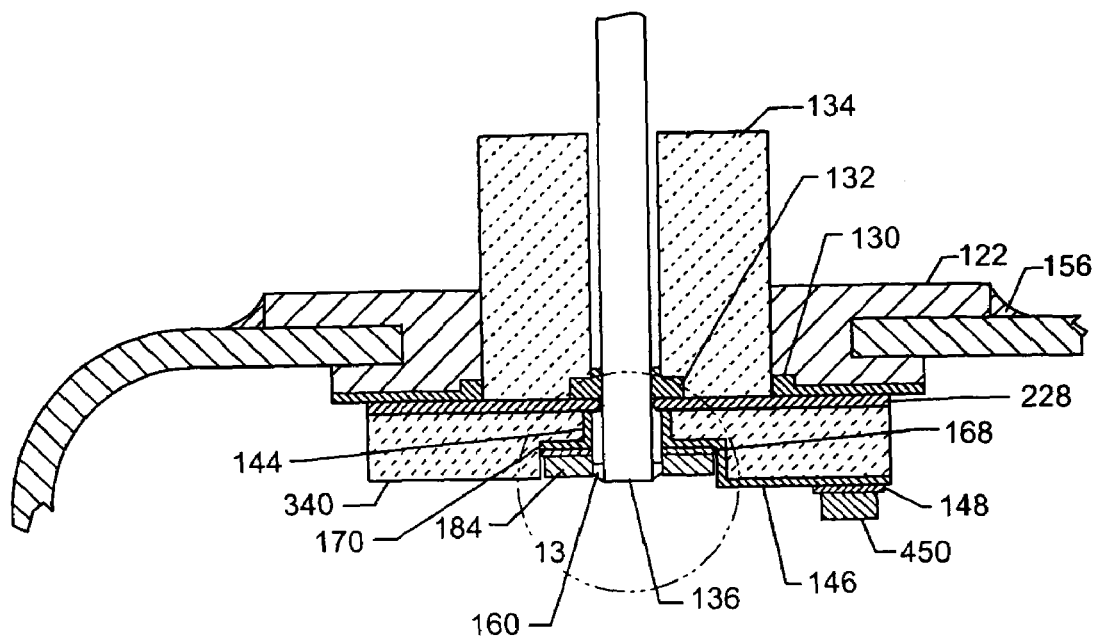
FIG. 12 is a fragmented cross-sectional view of the hermetic terminal of FIG. 2 with modifications.
Figure 13:
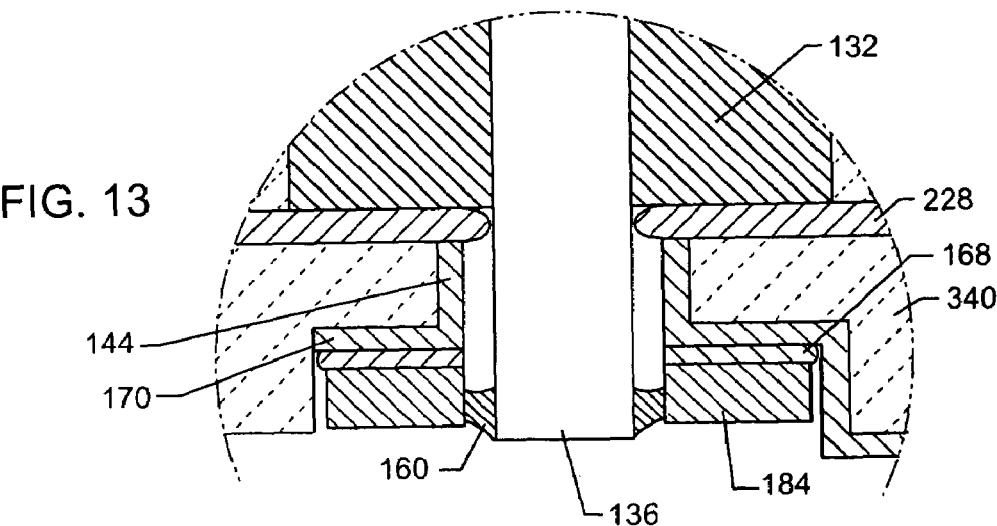
FIG. 13 is an enlarged, fragmented cross-sectional view of the area indicated by the number 13 in FIG. 12.

FIG. 12 is a cross-sectional view of the hermetic terminal of FIG. 2 modified with two improvements. As previously mentioned, it is highly desirable that all electrical connections that are in series with the input or output of an implantable medical device be of extremely high reliability. Accordingly, referring to FIG. 12, one can observe that there is a Kovar, Alloy 42 or equivalent metal insert ring 184 that is placed either on top of or into a counterbore of the alumina substrate 340. This is better understood by looking at the enlarged cross-section view of this same area of FIG. 12 in FIG. 13. According to FIG. 13, one can see the cross-section of the insert metal piece 184 which has been selectively plated with nickel and then pure gold. Ring 184 has been previously gold brazed 168 to the metallization 170 of the alumina ceramic substrate 340 making a solid mechanical and electrical connection. The terminal pin 136 is then attached by laser welding 160 to the metallic ring 184. Laser welding makes a very reliable and rugged electrical and mechanical joint in this important series connection.

Referring now back to FIG. 12, one can see that the metallization 144 on the inside diameter or via hole on the alumina substrate 340 is continuous as a circuit trace to 170 to 146 all the way to the wire bond pad area 148. The wire bond pad 450 is a metal block preferably of Alloy 42 or Kovar and is also undercoated with nickel and then overcoated with ultra-pure or soft gold suitable for lead wire bonding. It is well known in the art that laser welding or wire bonding is much more easily accomplished to a Kovar or Alloy 42 surface.

Figure 14:
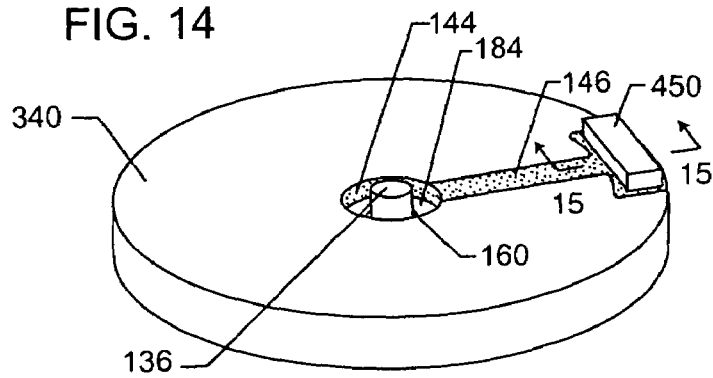
FIG. 14 is an inverted perspective view of the alumina substrate of FIG. 12.

FIG. 14 shows an inverted isometric view of the alumina substrate 340 of FIG. 12. In this view, one can easily observe the top of the insert ring 184, the tip of the terminal pin 136, the circuit trace 146 and the Kovar or Alloy 42 wire bond pad 450.

Figure 15:
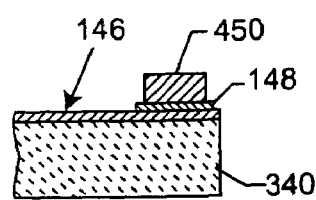
FIG. 15 is an enlarged, fragmented cross-sectional view taken along the line 15—15 of FIG. 14.

FIG. 15 is a cross-sectional view from FIG. 14 which better illustrates the mounting of the wire bond pad 450. As one can see, wire bond pad 450 has been electrically and mechanically attached to the circuit trace 146 using braze preform 148. This brazing operation would typically be performed on the alumina substrate 340 in a high temperature vacuum-brazing furnace. The braze joints 168 and 148 of FIG. 12, which attaches the ring 184 to the alumina substrate metallization 170 and the wire bond pad 450 to the alumina substrate 340 metallization 146 would typically be done in a vacuum brazing furnace re-flow operation.

Referring once again to FIG. 12, a similar electrical connection from the insert ring 184 to the terminal pin 136 is formed by the laser welding material 160. This laser weld also burns through any surface oxide on niobium, tantalum, or titanium pins and the like, thereby making a highly reliable electrical connection from the pin 136 to the ring 184 which has been previously gold brazed to the surface metallization 170, of substrate 340.

In summary, the novel assembly with substrate as described in FIG. 12 has a number of advantages, including the obvious one of having highly reliable brazed electrical connections, and being suitable for wire bonding, but also suitable for use with literally any type of biocompatible terminal pin 136.

Figure 16:
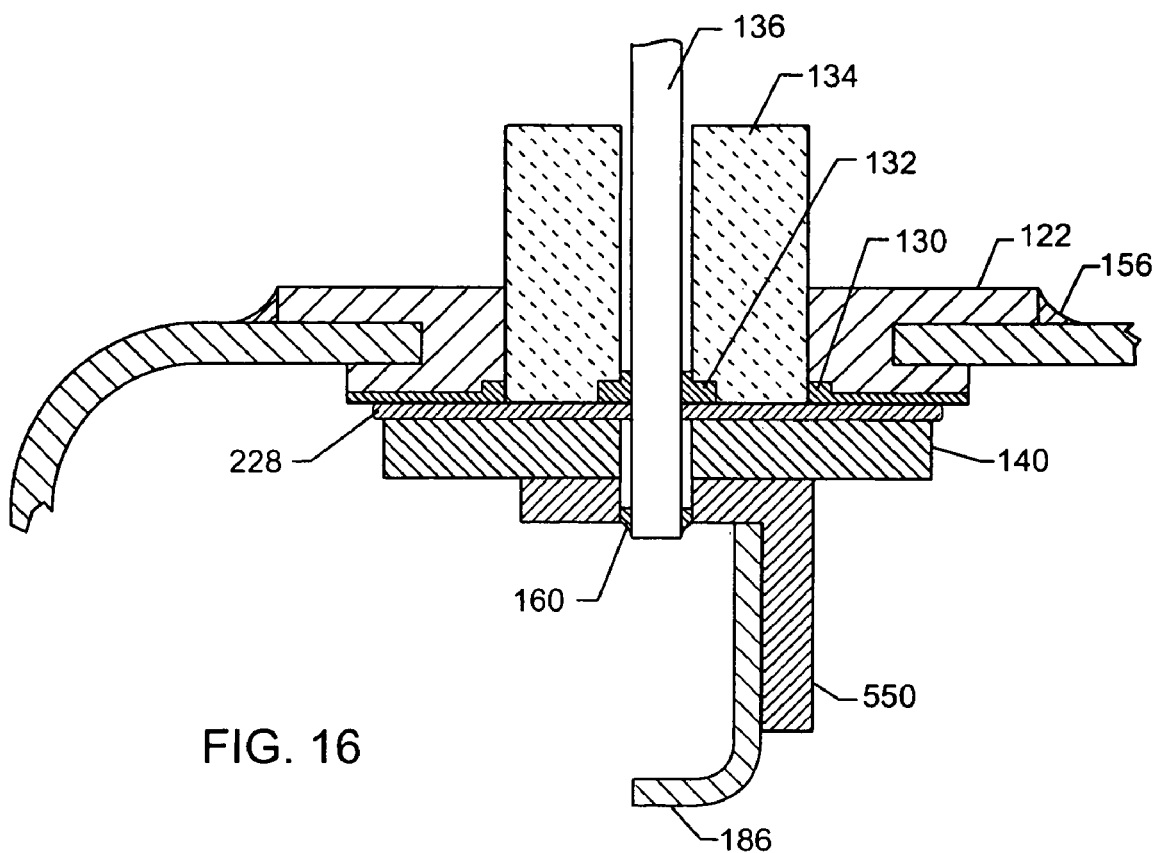
FIG. 16 is a fragmented cross-sectional view similar to FIG. 2, illustrating the use of an L-shaped wire bond cap.
Figure 17:
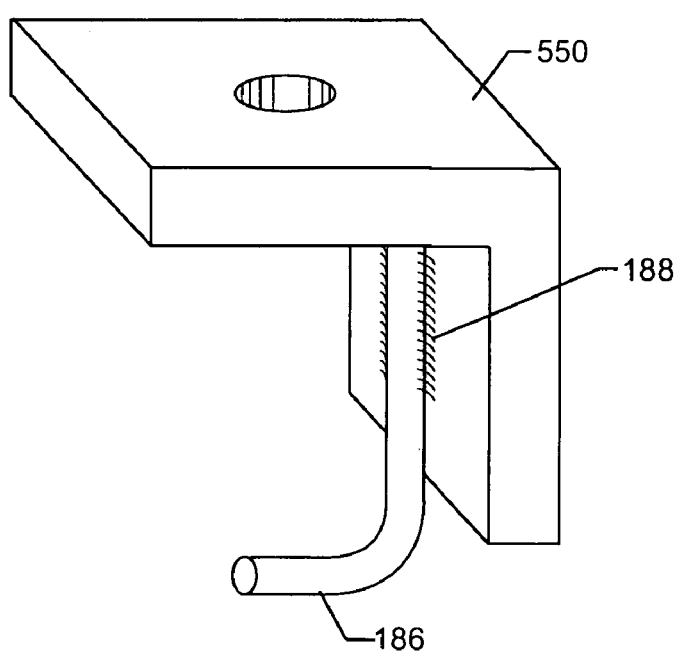
FIG. 17 is a perspective view of the attachment of a lead wire to the L-shaped wire bond pad of FIG. 16.

FIG. 16 illustrates a cross-sectional view of the present invention with an L-shaped wire bond cap 550. This wire bond cap 550 is typically Kovar or Alloy 42 and is gold plated. Also shown in FIG. 16 is the cross-section of a wire bonded lead wire 186. The attachment of lead wire 186 to the L-shaped wire bond pad 550 is better seen in isometric view FIG. 17. As one can see, lead wire 186, which is routed to internal implanted medical device circuitry, has been wire bonded in the area shown as 188 to the wire bond pad 550. It is typical in the art that 186 be a small diameter, pure gold or aluminum wire, such as a wire 0.005 inches in diameter. The wire bond connection 188 is typically formed by ultrasonic or thermosonic processes that are very well known in the art.

Figure 18:
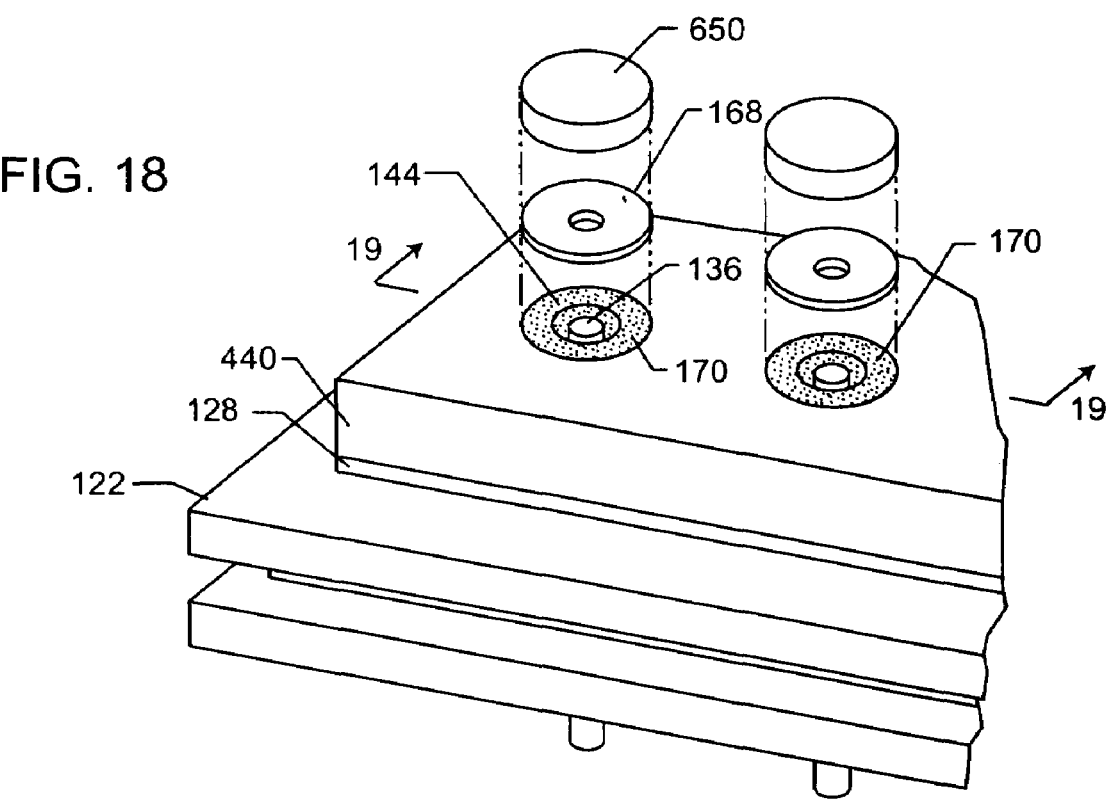
FIG. 18 is a fragmented perspective and partially exploded view of a bipolar feedthrough terminal assembly with wire bond caps.
Figure 19:
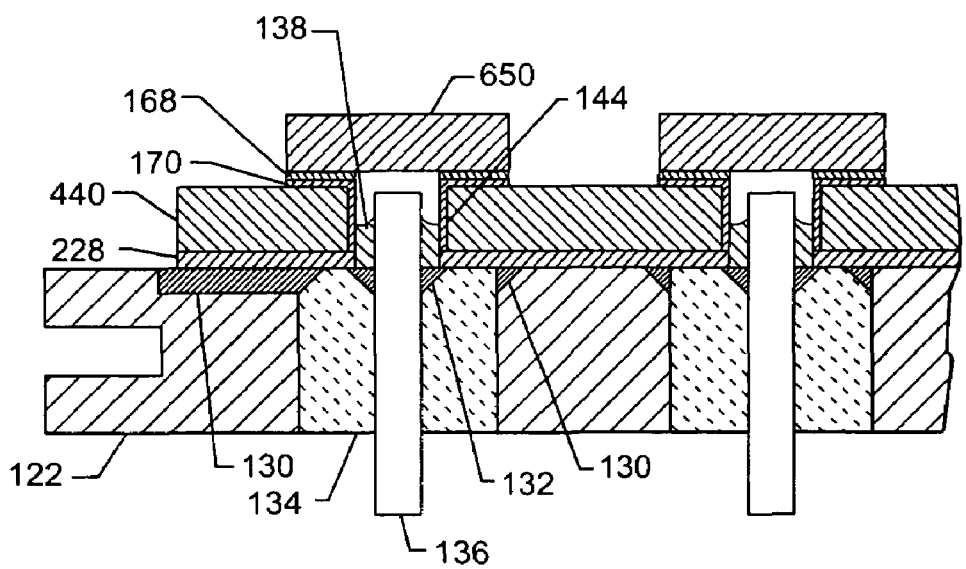
FIG. 19 is an enlarged, fragmented cross-sectional view taken generally along the line 19—19 of FIG. 18.

FIG. 18 illustrates the top view of a bipolar feedthrough assembly of the present invention. In this embodiment, exploded away circular wire bond pads 650 are placed over the top of the feedthrough holes of substrate 440 for convenient attachment of lead wires 186 (not shown). This is better understood by observing the cross-section of FIG. 18 illustrated in FIG. 19. As shown in FIG. 19, a circular wire bond pad 650 is attached to the top surface via metallization 170 of the ceramic substrate 440. The attachment of the circular wire bond pad 650 is by gold brazing 168 to the top metallization 170 of the alumina substrate 440. In this case, the terminal pin 136, which comes from the hermetic terminal consisting of 122, 130, 132,136 and 134, is shortened as shown. The alumina substrate 440 is co-bonded using a nonconductive polyimide preform 228 to the top surface of the hermetic terminal. The electrical connection material 138 is typically a conductive thermal-setting polymer, such as a conductive polyimide, solder or the like. The electrical connection material 138 electrically connects the inside diameter or via hole metallization 144 of the substrate 440 to the terminal pin 136.

Figure 20:
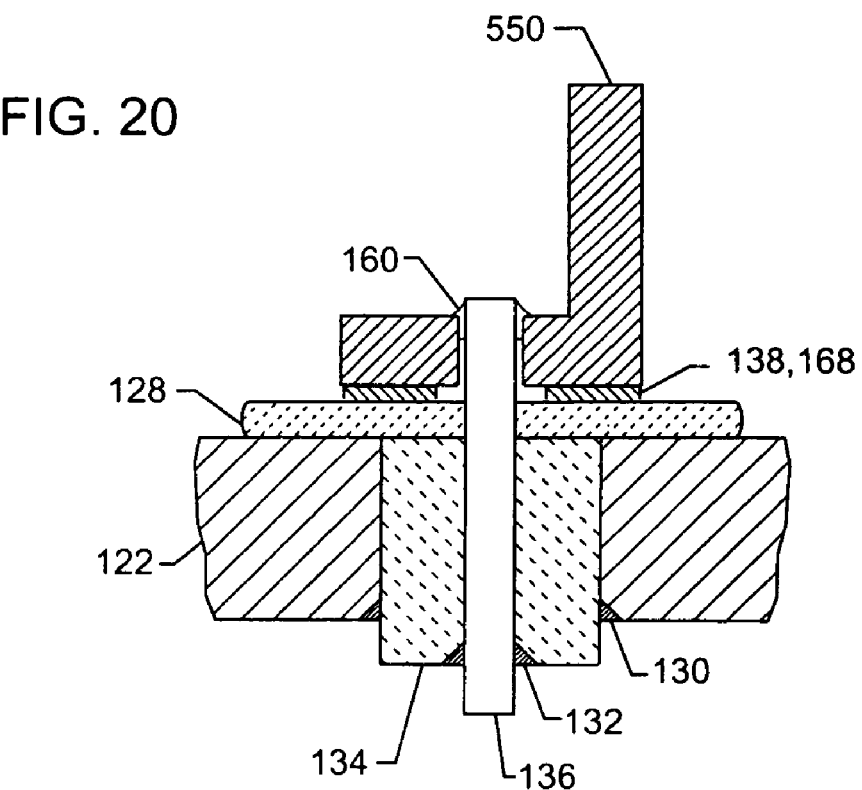
FIG. 20 is a sectional view of an alternative wire bond pad arrangement in comparison with that illustrated in FIG. 19.

FIG. 20 shows an alternative embodiment to that previously described in FIG. 16. In both cases, there is an L-shaped wire bond pad 550. A laser weld connection 160 is formed between terminal pin 136 and the wire bond pad 550 as shown.

Figure 21:
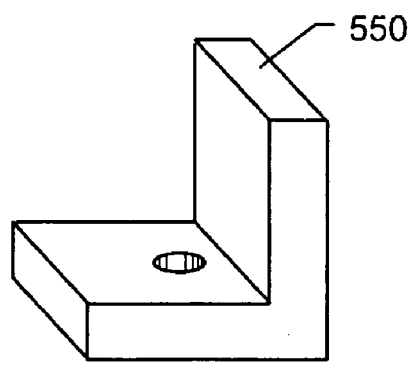
FIG. 21 is a perspective view of the L-shaped wire bond pad of FIG. 20.
Figure 22:
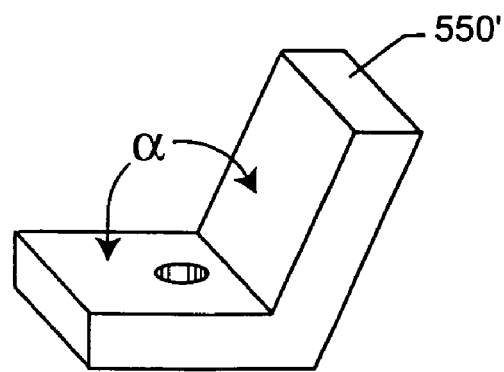
FIG. 22 is a perspective view similar to FIG. 21, illustrating the configuration of an alternative wire bond pad.
Figure 32:
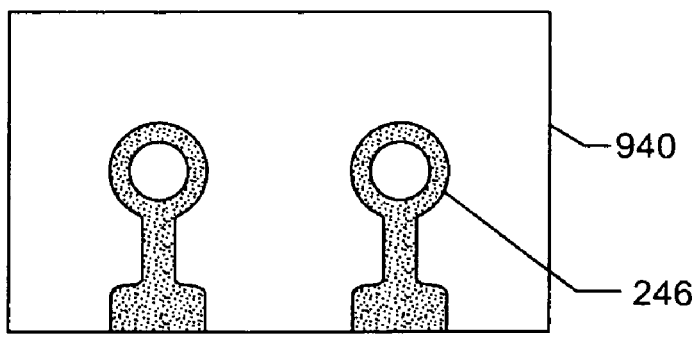
FIG. 32 is a cross-sectional view through the multi-layer substrate taken generally along the line 32—32 of FIG. 31.

FIG. 21 is an isometric view of the L-shaped wire bond pad 550, previously described in FIG. 20. FIG. 32 is a similar wire bond pad 550' as described in FIG. 21, except that it is angled ($\propto$) to line up with the geometry or architecture of the internal circuits of the implanted medical device. As shown in FIG. 22, any convenient angle ($\propto$) can be used.

Figure 23:
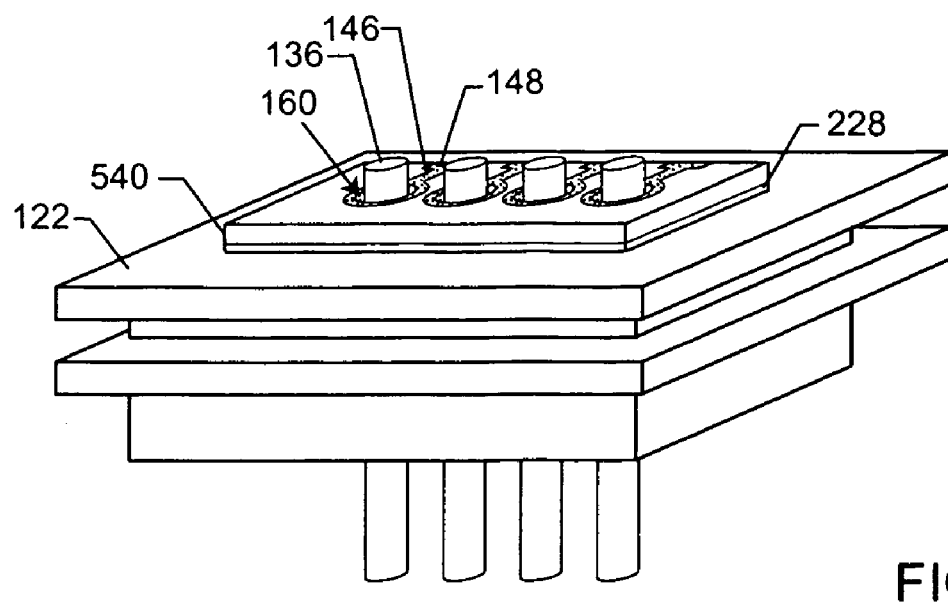
FIG. 23 is a perspective view of a quadpolar hermetic feedthrough terminal assembly.

FIG. 23 illustrates a quadpolar alumina substrate 540 that has been co-bonded to the top of the ferrule 122 using insulating adhesive material 228. Highly reliable laser weld connections 160 are used to connect the inside diameter or via hole metallization 144 (not shown) of the alumina ceramic substrate 540 to the four terminal pins 136. As one can see, there are circuit traces 146 as part of the alumina substrate 540 that connect to wire bond pad areas 148. As previously mentioned, such circuit traces 146 with selectively metallized via holes are very typical in the art and are in very common use with a number of substrate materials, including aluminum oxide, alumina, fiberglass, polyimide and many others.

Figure 24:
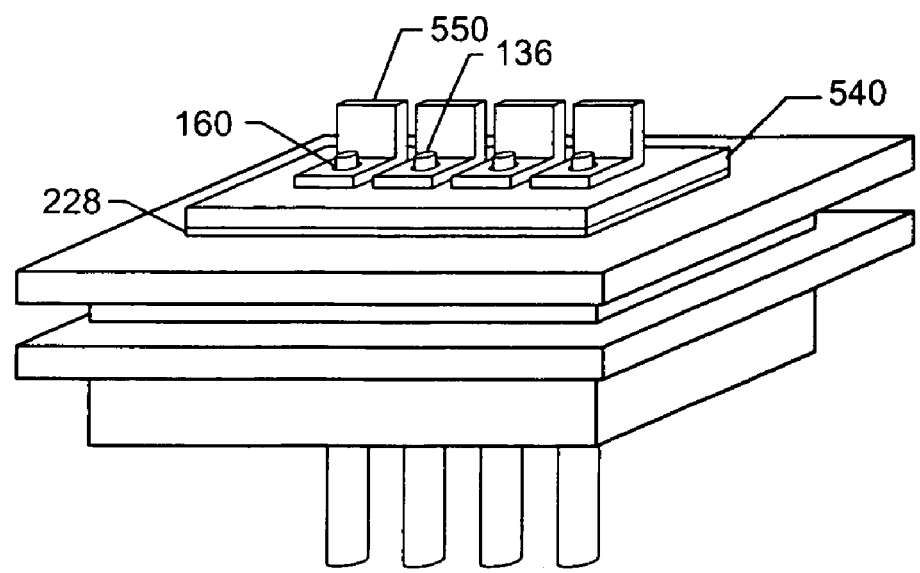
FIG. 24 is a perspective view similar to FIG. 23, illustrating the use of L-shaped wire bond pads.

FIG. 24 illustrates an alternative embodiment of FIG. 23 showing L-shaped wire bond pads 550. As previously described in other FIGURES, these wire bond pads are gold brazed to metallization 170 (not shown) on the top of the alumina ceramic substrate 540. A laser weld connection 160 is then made from the terminal pins 136 to each of the L-shaped wire bond pads 550. It would be obvious to one skilled in the art that a variety of shapes of wire bond pads would be available. The alumina substrate 540 as illustrated in FIG. 23 and FIG. 24, is co-bonded to the top of the ferrule 122 using a suitable insulator washer 228, which in the preferred embodiment, would be an adhesive coated polyimide as described in FIG. 3 which would be cured at high temperature. Polyimide is an ideal polymer in this case because it forms a ring molecule which tends to absorb stresses. An epoxy or similar material could also work.

Figure 25:
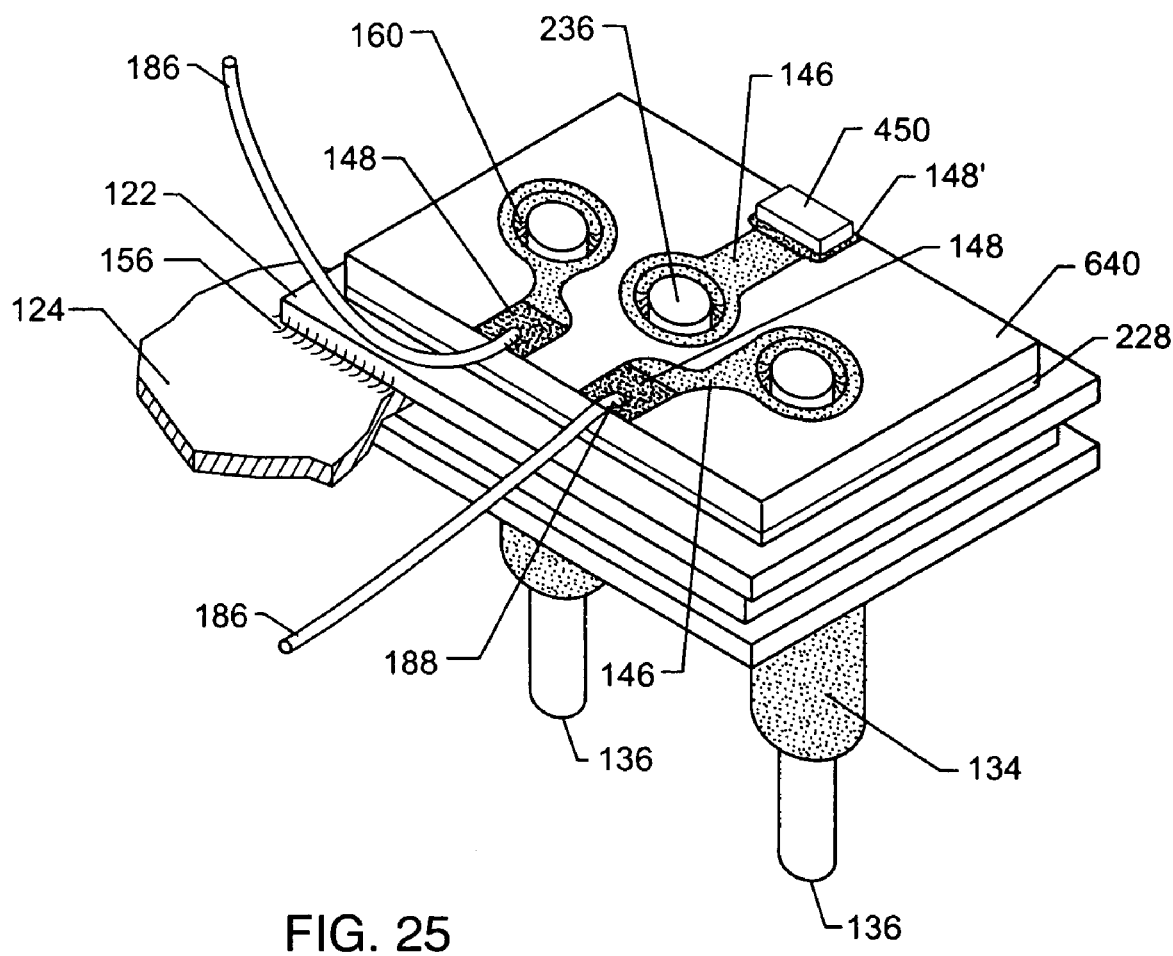
FIG. 25 is a perspective view of a hermetic terminal within an internally grounded pin and with a co-bonded wire bond substrate.

FIG. 25 illustrates a bipolar wire bond substrate with an additional grounded wire bond pad 450. Ferrule 122 is typically of titanium and has been designed to be laser welded into the housing of an implantable medical device 124, such as a cardiac pacemaker, which is shown as a cut away of the housing of a cardiac pacemaker and having a laser weld 156 which makes a mechanical and hermetic connection to the hermetic terminal ferrule 122. Alumina substrate 640 has been co-bonded using nonconductive insulating adhesive material 228 to the ferrule 122 and insulators 134. Also illustrated in FIG. 25 are two alternative circuit traces 146 and wire bond pads 148 and 148'. Wire bond pad 450 is shown connected to the grounded lead bond pad 148' as suitable for a more reliable wire bond connection. A lead wire 186 is wire bonded 188 directly to the circuit trace wire bond pad area 148 of the alumina ceramic substrate 640. In the preferred embodiment, the inside diameter via hole metallization 144 (not shown) of the alumina substrate 640 would be connected to the terminal pin 136 and 236 by laser weld material 160. Other suitable (but less reliable) connections could be made using solder, thermal-setting conductive adhesives or the like. In general, a laser weld or braze makes for a much higher reliability in series electrical connection.

Figure 26:
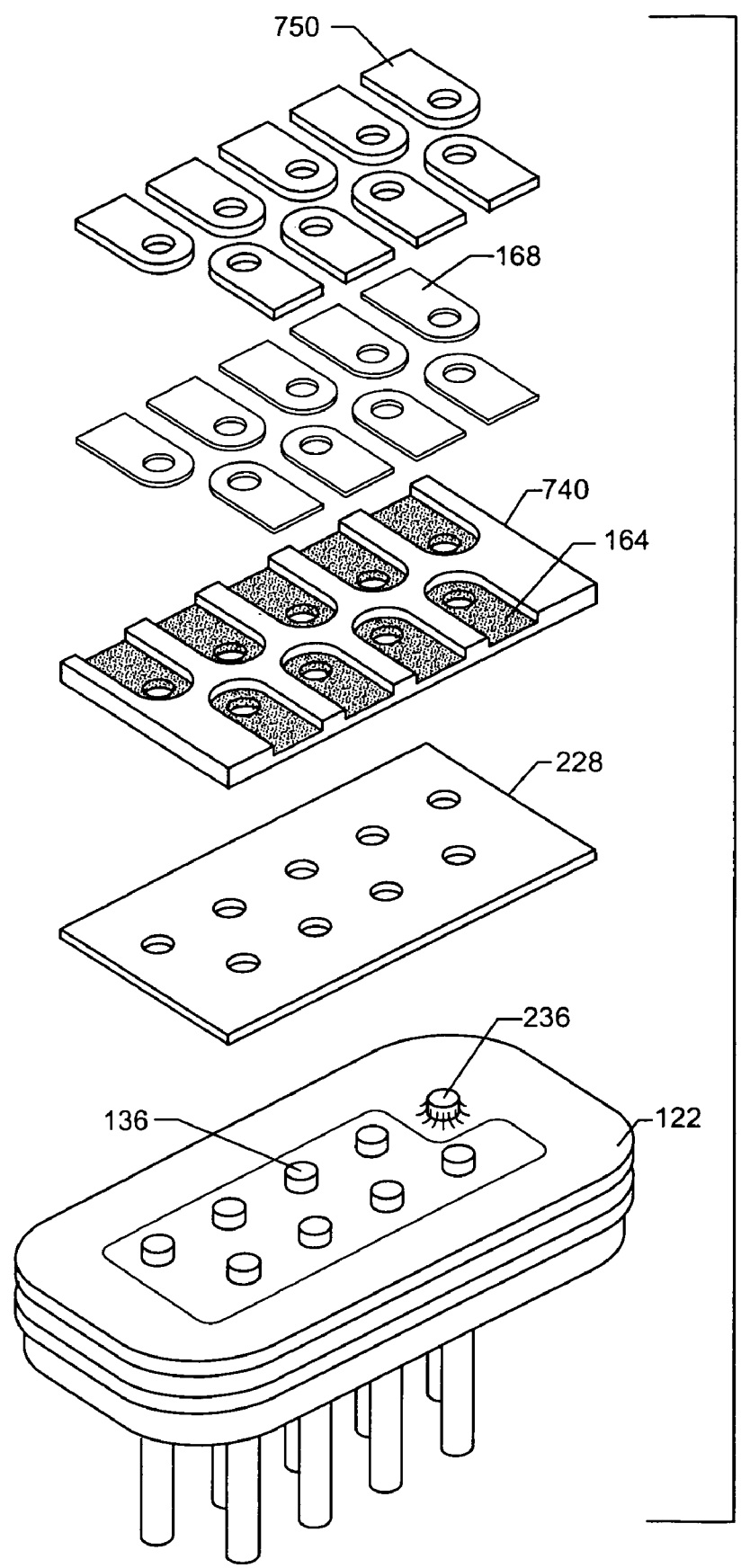
FIG. 26 is an exploded perspective view of a dual inline 9-pole feedthrough hermetic terminal embodying the present inventions with one of the pins grounded.

FIG. 26 illustrates an exploded view of a dual inline 9-pole feedthrough hermetic terminal of the present invention. In the exploded view, one can see the wire bond pads 750, which are typically of gold plated Kovar or the like. The alumina substrate 740 has convenient recesses and metallized areas 164 (typically of gold or nickel coated tungsten) suitable for metallurgical connection via gold brazing material or preforms 168 to the wire bond pads 750. An adhesive coated polyimide nonconductive preform washer 228 bonds the alumina substrate 740 to the ferrule 122. Ground pin 236 has been solidly welded, gold brazed or machined into the metallic ferrule 122. All of the other pins 136 are in nonconductive relationship with the ferrule 122 as previously described in the prior art.

Figure 27:
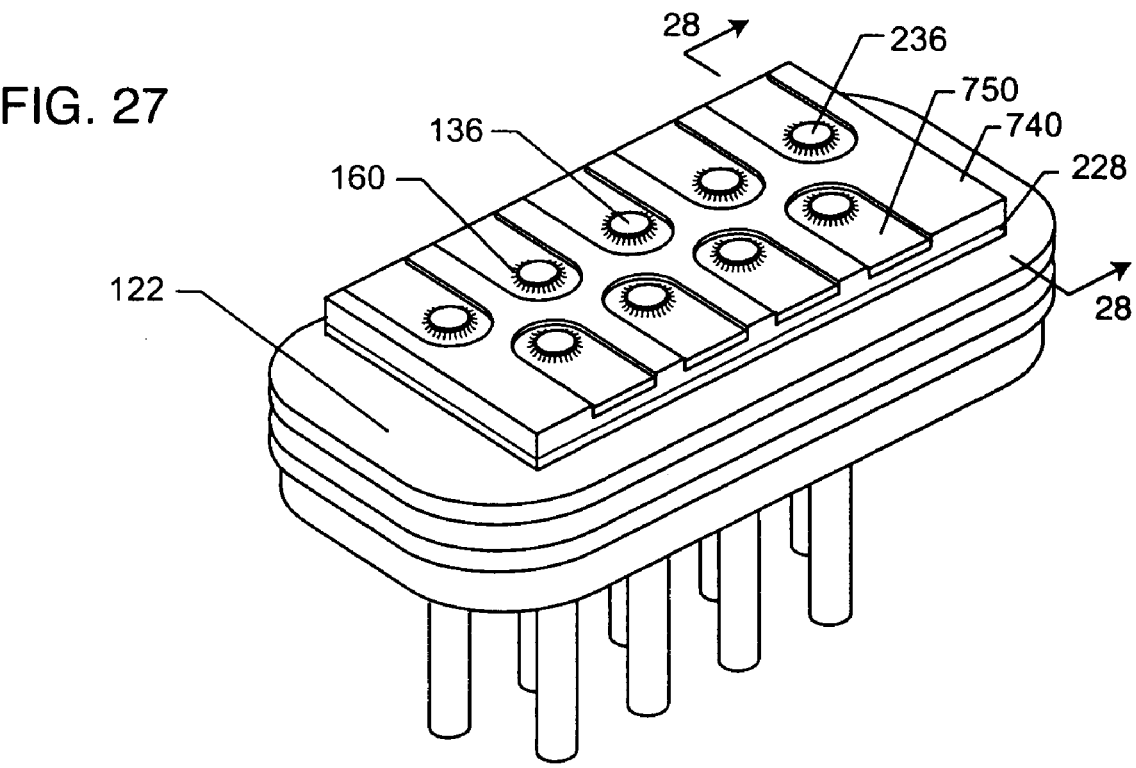
FIG. 27 is a perspective view of the assembled 9-pole feedthrough hermetic terminal of FIG. 28.

FIG. 27 illustrates a perspective view of the completed assembly of FIG. 26. As one can see, convenient wire bond attachment can be made to the wire bond pads 750. It should also be noted that there are a number of alternative shapes including L-shapes that could be used for these wire bond pads. Ground pin 236 provides a convenient method for grounding AIMD circuitry or for using the AIMD housing as an electrode (hot can).

Figure 28:
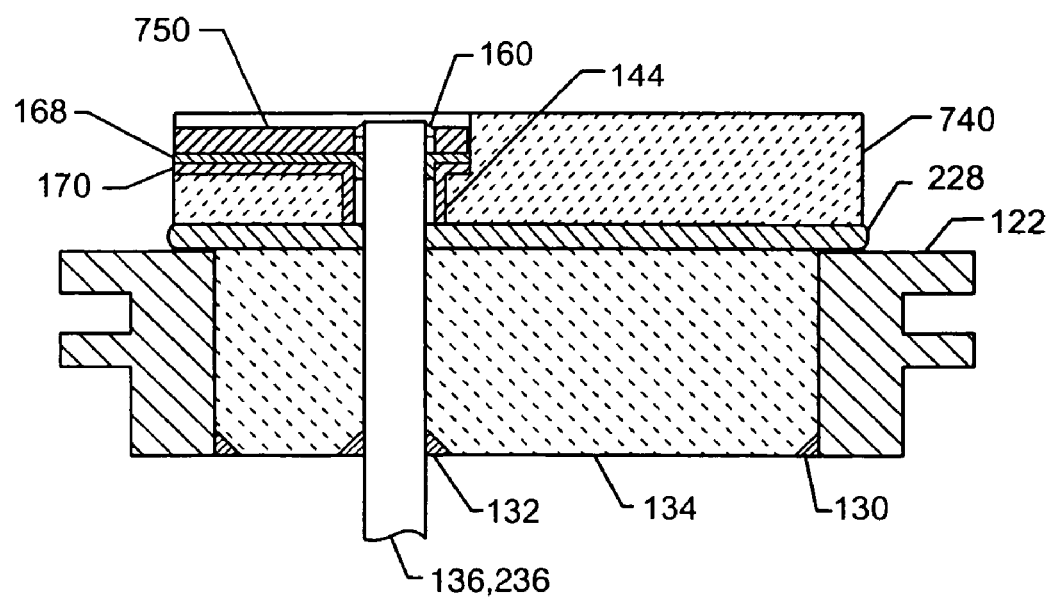
FIG. 28 is an enlarged cross-sectional view taken generally along the line 28—28 of FIG. 27.

FIG. 28 is a cross-sectional view of the 9-pole internally grounded feedthrough assembly of FIG. 27. As one can see in the cross-sectional view, laser weld connection 160 is made between each wire bond pad 750 and the corresponding terminal pin 136 or 236.

Figure 29:
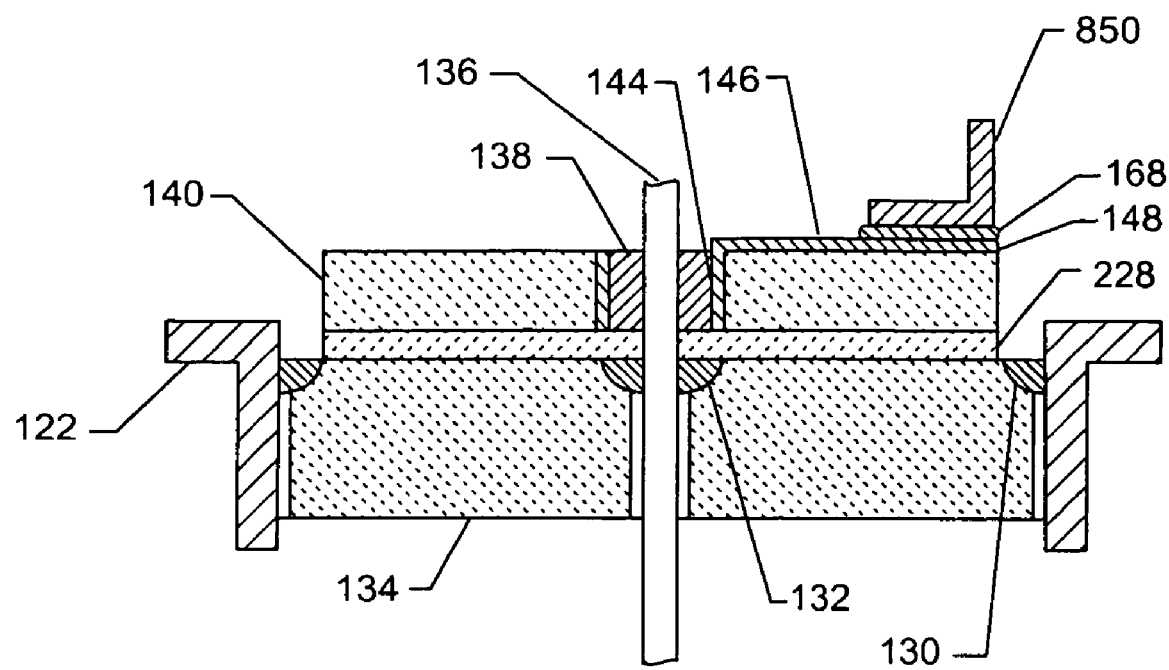
FIG. 29 is a cross-sectional view illustrating a unipolar feedthrough including a substrate co-bonded directly to the top surface of the insulator in accordance with the present invention.
Figure 30:
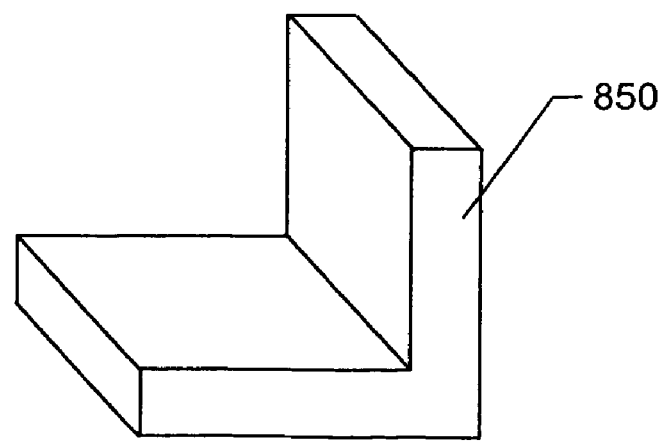
FIG. 30 is a perspective view of the L-shaped wire bond pad shown in FIG. 29.

FIG. 29 illustrates the substrate 140 that has been co-bonded 228 directly to the top surface of the insulator 134. In this case, an L-shaped wire bond pad 850, as shown in FIG. 30, has been gold brazed 168 to the top surface metallization 148 of the alumina ceramic substrate 140. There is a continuous electrical connection through top metallization 146 to the inside diameter metallization of the via hole 144. Electrical connection material 168 can be of gold braze, solder, thermal-setting conductive adhesive and the like. The terminal pin 136 is thereby electrically connected to the inside diameter metallization 144 of the alumina ceramic substrate 140.

Figure 31:
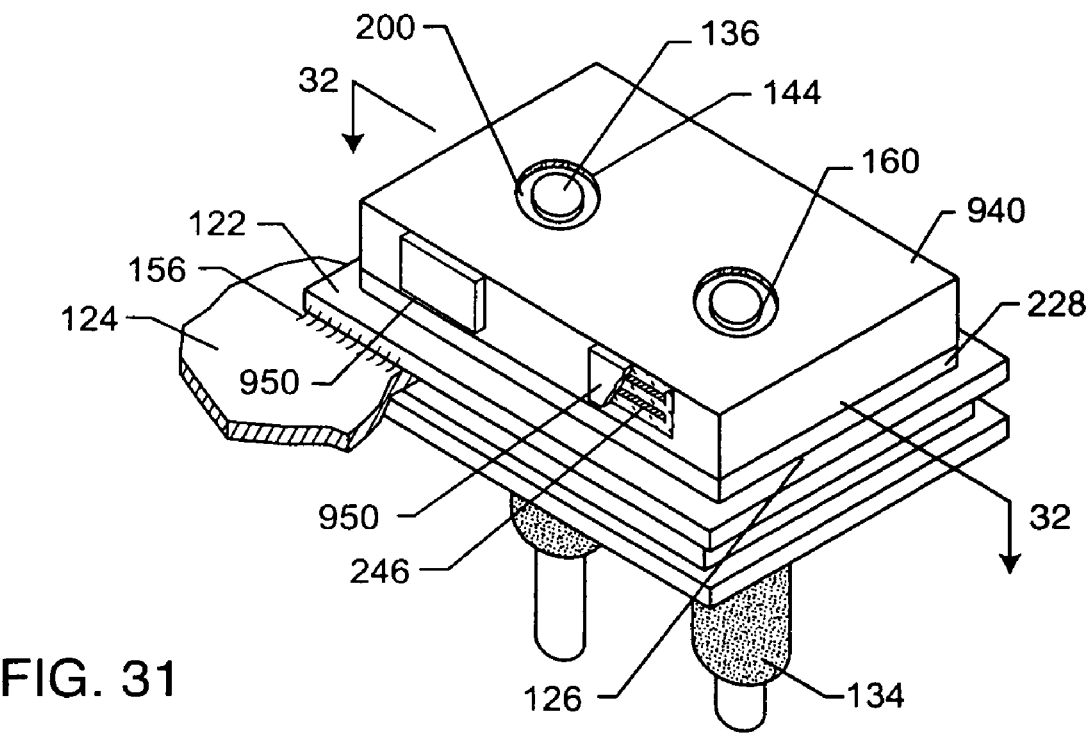
FIG. 31 illustrates yet another hermetic terminal embodying the invention, wherein a multi-layer substrate containing embedded circuit traces is utilized.

FIG. 31 illustrates a multi-layer substrate 940 having embedded circuit traces 246 at various levels within the laminated and sintered ceramic substrate 940. Multi-layer circuit boards and substrates are well known in the art and are used for a variety of purposes. In a preferred embodiment, substrate 940 is of alumina ceramic or fosterite or similar ceramic material. However, multi-layer substrate 940 could be constructed of any commonly used circuit board materials, including plastics, fiberglass, polyimides and the like.

FIG. 32 is a cross-sectional view of the one or more multi-layer alumina ceramic substrate 940 taken generally along the section line 32—32, as shown. FIG. 32 illustrates two embedded circuit traces 246 which are typically of gold, molybdenum, tungsten or other suitable metallic conductor.

Referring now back to FIG. 31, the circuit traces 246 are shown exposed on the edge of the bipolar substrate 940 underneath the partial cutaway view of the right-hand wire bond pad 950. Wire bond pad 950 is typically attached by gold brazing as previously described herein. In FIG. 31, there are two embedded circuit trace layers 246 contained within the substrate 940. In this particular embodiment, both circuit traces 246 are geometrically identical, redundant, and in parallel. Depending upon the implantable device application, there could be one, two or many more of the FIG. 32 parallel embedded circuit traces 246 as shown in FIG. 31. For example, in a cardiac pacemaker, the pacing and biological sensing currents are relatively small. Accordingly, the DC resistance of these circuit traces is not particularly critical. Therefore, in the case of a cardiac pacemaker, only one or two parallel circuit traces 246, as illustrated in FIG. 31, would be required. However, in an implantable cardioverter defibrillator, very high currents are produced when the cardioverter defibrillator or ICD delivers high voltage discharge therapy to the heart. Accordingly, any voltage drop or energy loss across the resistance of the embedded circuit traces 246 would be problematic. Therefore, in the case of an ICD application, up to 10 or even more circuit traces 246 could be required. The resistance of an individual circuit trace 246 also depends upon its thickness, width, resistivity and length.

Referring now back to FIG. 31, in a preferred embodiment, the contact to the terminal pin 136 would be by way of an embedded or surface (not shown) ring 200 and highly reliable laser weld connection 160 to terminal pin 136.

Figure 33:
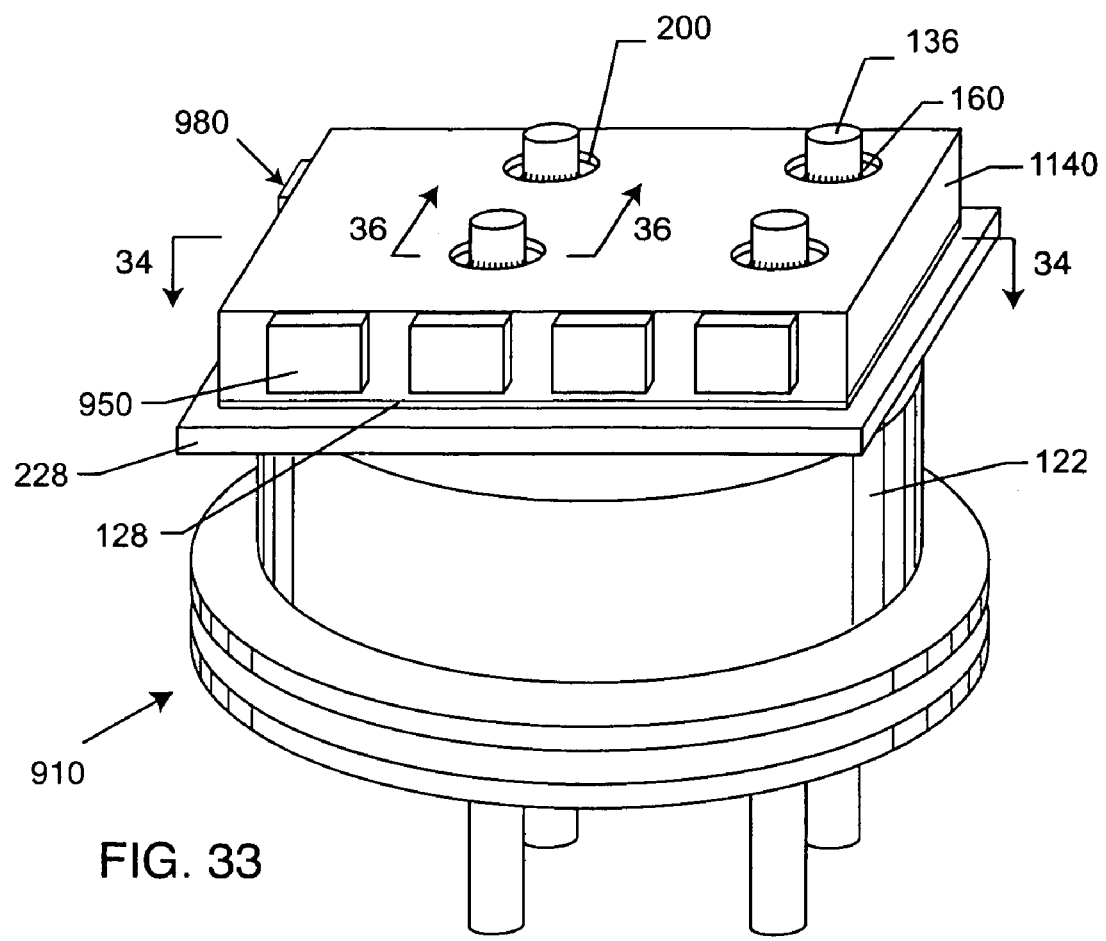
FIG. 33 is a perspective view illustrating a round quadpolar hermetic feedthrough assembly with a rectangular circuit substrate attached by co-bonding.

FIG. 33 illustrates a round quadpolar feedthrough capacitor 910 assembly with a rectangular circuit substrate 1140 of the present invention attached by co-bonding 128 and 228. There are a number of reasons why implantable device manufacturers often prefer circular geometry for the hermetic seal. One is the fact that these are easier to laser weld into the overall housing or can 124 (not shown) of an implantable medical device. However, when it comes to connecting the terminal pin 136 from internal circuits to a round feedthrough this is often not the optimal geometry. Hybrid circuit boards that are used in implantable medical devices are usually rectilinear in dimension. Accordingly, having wire bond pads 950 that are lined up along straight lines are often preferred. The embodiment shown in FIG. 33 solves this problem by adding a rectangular multi-layer substrate 1140 with wire bond pads 950 as shown.

Figure 34:
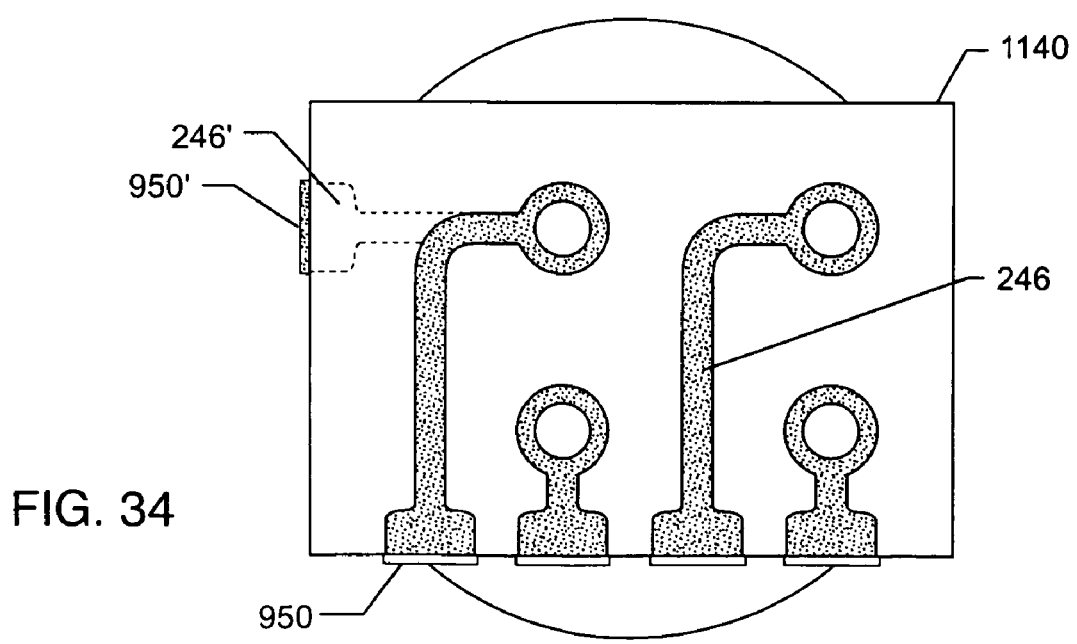
FIG. 34 is a sectional view taken generally along the line 34—34 of FIG. 33, illustrating one of four internal circuit traces at one level of the substrate.

FIG. 34 is a top down cross-section showing one of four internal circuit traces 246 at one level of the substrate 1140 of FIG. 33. As previously mentioned, there can be one or many of these identical circuit trace layers all acting in parallel within the multi-layer substrate 1140. An optional location for the circuit trace and wire bond pad 246' and 950' is shown to illustrate that these circuit traces can be run in any direction in which ones imagination allows. These are usually laid down by high production volume metal cladding, silk-screening or similar metal deposition methods.

Figure 35:
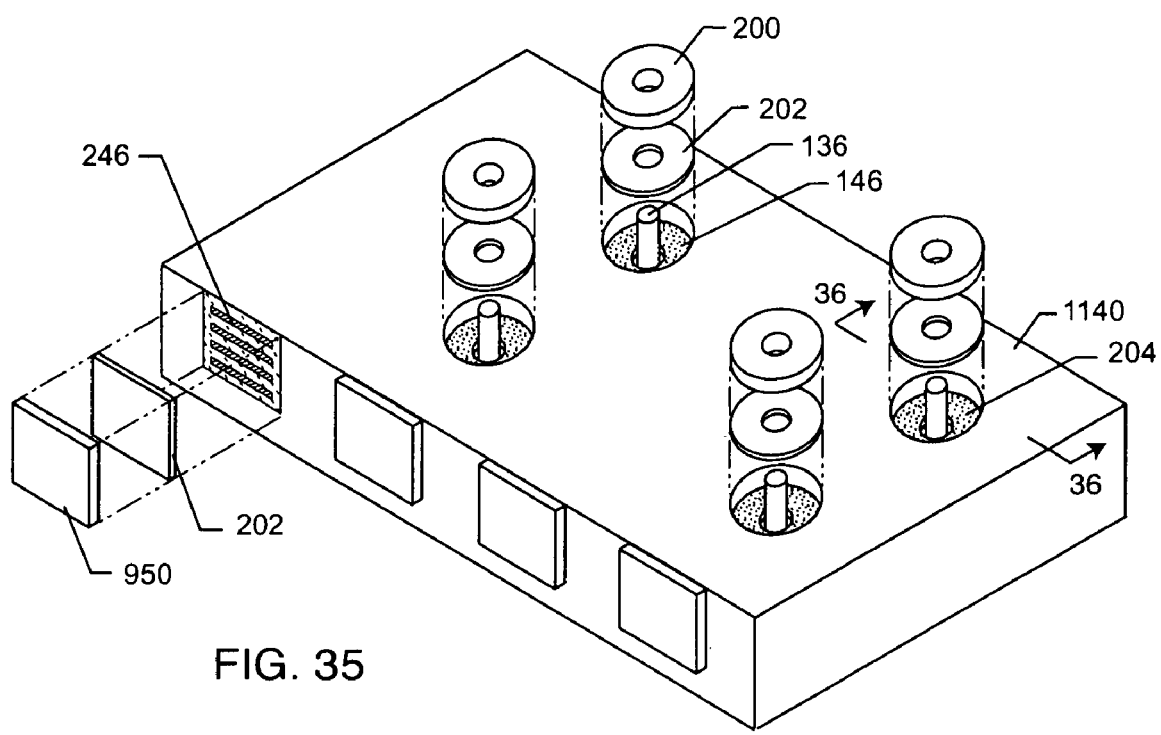
FIG. 35 is an enlarged and partially exploded perspective view of the alumina substrate of FIG. 33, illustrating the methodology of application of the wire bond pads to the alumina substrate.

FIG. 35 illustrates the methodology of application of the wire bond pads 950 to the alumina substrate 1140 of FIG. 33. As one can see, in this case there are four parallel embedded circuit traces 246. As mentioned, these act in parallel reducing the overall DC resistance and inductance of the circuit. The wire bond pad 950 is typically of Kovar, Alloy 42 or similar construction which has been nickel and then gold plated. A gold preform 202 is used to attach the Kovar pad 950 to metallization which covers the circuit traces 246 (metallization not shown). This operation is typically performed in a gold brazing furnace. FIG. 35 also illustrates a metallic ring 200 which is gold brazed to metallization 146 on the inside diameter surface of the counterbore 204 of the alumina substrate 1140. As previously described, and as illustrated in FIG. 33, the most reliable connection is a laser weld 160 between the terminal pin 136 and the metallic ring 200.

Figure 36:
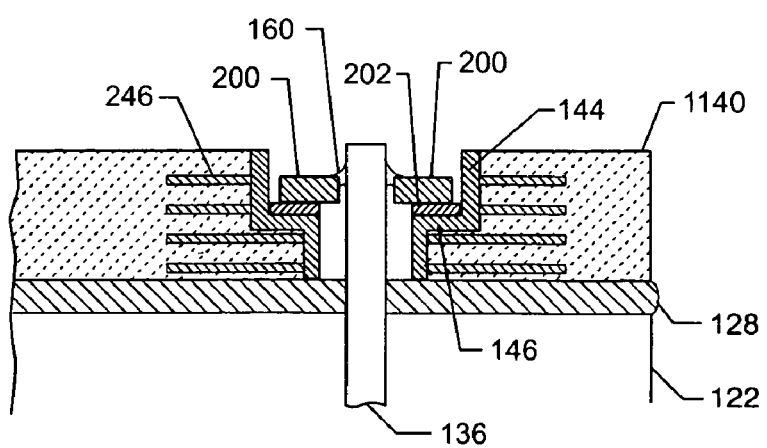
FIG. 36 is an enlarged, fragmented cross-sectional view taken generally along the line 36—36 of FIG. 35.

FIG. 36 is a cross-sectional view of this metallic ring 200 shown attached to the terminal pin 136 with a laser weld connection 160. The cross-sectional view of FIG. 36 also shows the end view of the four embedded circuit traces 246 which electrically connect to the inside diameter via hole metallization 144 and 146. As mentioned, the metal ring 200 would typically be of Kovar or Alloy 42 and gold brazed 202 to the via hole metallization 146.

Figure 37:
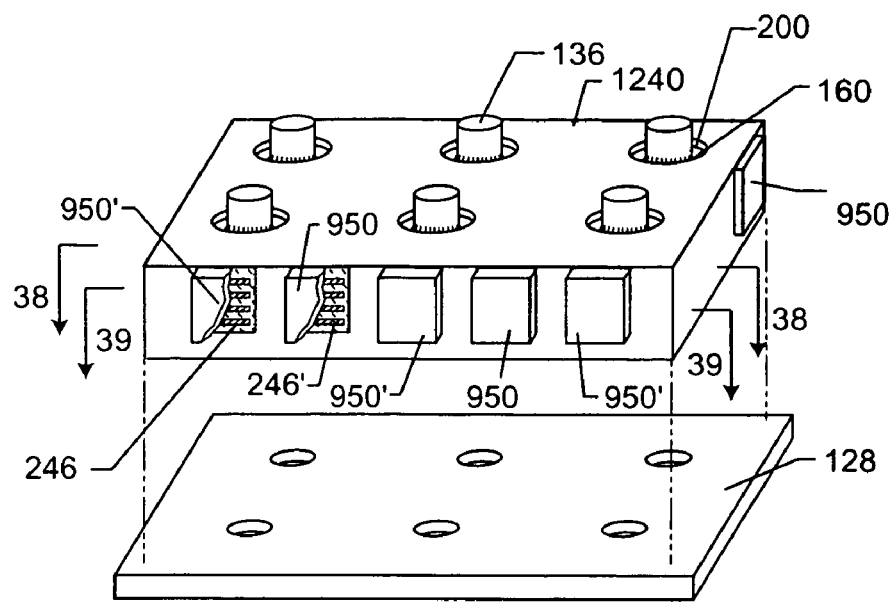
FIG. 37 is an exploded perspective view of a rectangular hexpolar substrate, in accordance with the present invention.

FIG. 37 illustrates a rectangular hexpolar substrate 1240 of the present invention. As shown, there are a total of six wire bond pads 950 and 950' shown in various locations around the perimeter of the substrate 1240. As previously described, the substrate 1240 is designed to be co-bonded using an insulating washer 128 to the top surface of the ferrule 122. The terminal pins 136, as shown in FIG. 37, are shown broken off in the substrate 1240 for illustrative purposes only and, of course, would actually protrude upward from a hermetic feedthrough terminal (not shown) of an implantable medical device. These terminal pins 136, in the preferred embodiment, would be attached to embedded or surface (not shown) rings 200 as previously described in FIGS. 35 and 36 with attachments 160 by laser welding.

Figure 38:
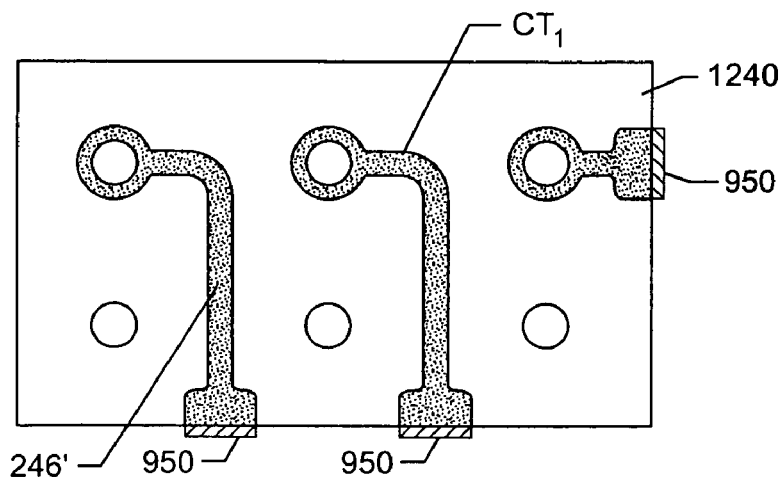
FIG. 38 is a cross-sectional view through the substrate taken generally along the line 38—38 of FIG. 37.
Figure 39:
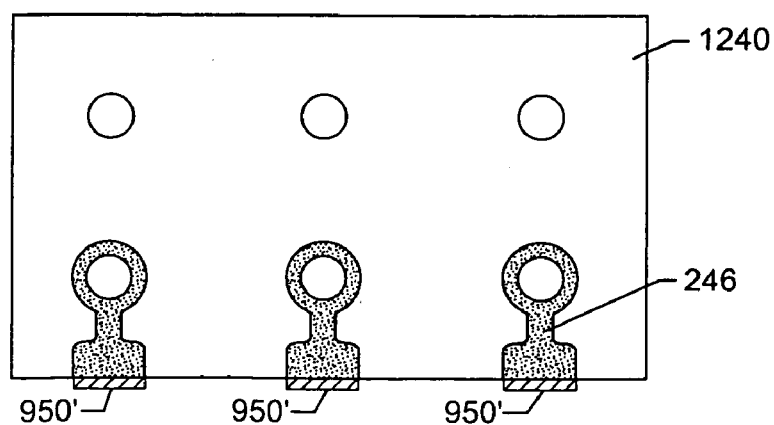
FIG. 39 is a cross-sectional view taken generally along the line 39—39 of FIG. 37.

A novel aspect of the multi-layer substrate 1240 shown in FIG. 37, is that its embedded circuit traces 246 and 246' need not be the same on different substrate levels. For example, FIG. 38 illustrates the circuit trace 246' on a first cross-section level of the substrate 1240 FIG. 37. FIG. 39 illustrates the circuit traces 246' on a different level. As previously mentioned, a number of these embedded circuit traces 246 and 246' can be placed in parallel to lower the overall DC resistance. For example, there might be five layers 246 in parallel to handle the output of an implantable defibrillator and only one layer 246' to handle the cardiac sensing and pacing currents which would be of very low current. As one can see, having different geometries on different circuit trace layers, allows one great latitude and flexibility in designing a hermetic terminal for an implantable medical device. This is particularly important in an implantable cardioverter defibrillator where voltages are quite high. In this regard, adjusting the number, thickness and length of the circuit traces on differing levels is utilized to adjust the overall resistance and current handing capability of the active implantable medical device. Using the techniques described, in FIGS. 38 and 39, one can be sure the circuit traces 246 and 246' are placed widely apart, but at various levels within the substrate 1240 so that they do not have any chance of arcing or shorting out.

Referring now back to FIG. 37, one can see that the wire bond pads 950' are attached to circuit traces 246 as shown in FIG. 39, and wire bond pads 950 are attached to circuit traces 246' as shown in FIG. 38. There are literally an infinite number of possible circuit trace geometries on various levels as will be obvious to one skilled in the art.

Figure 40:
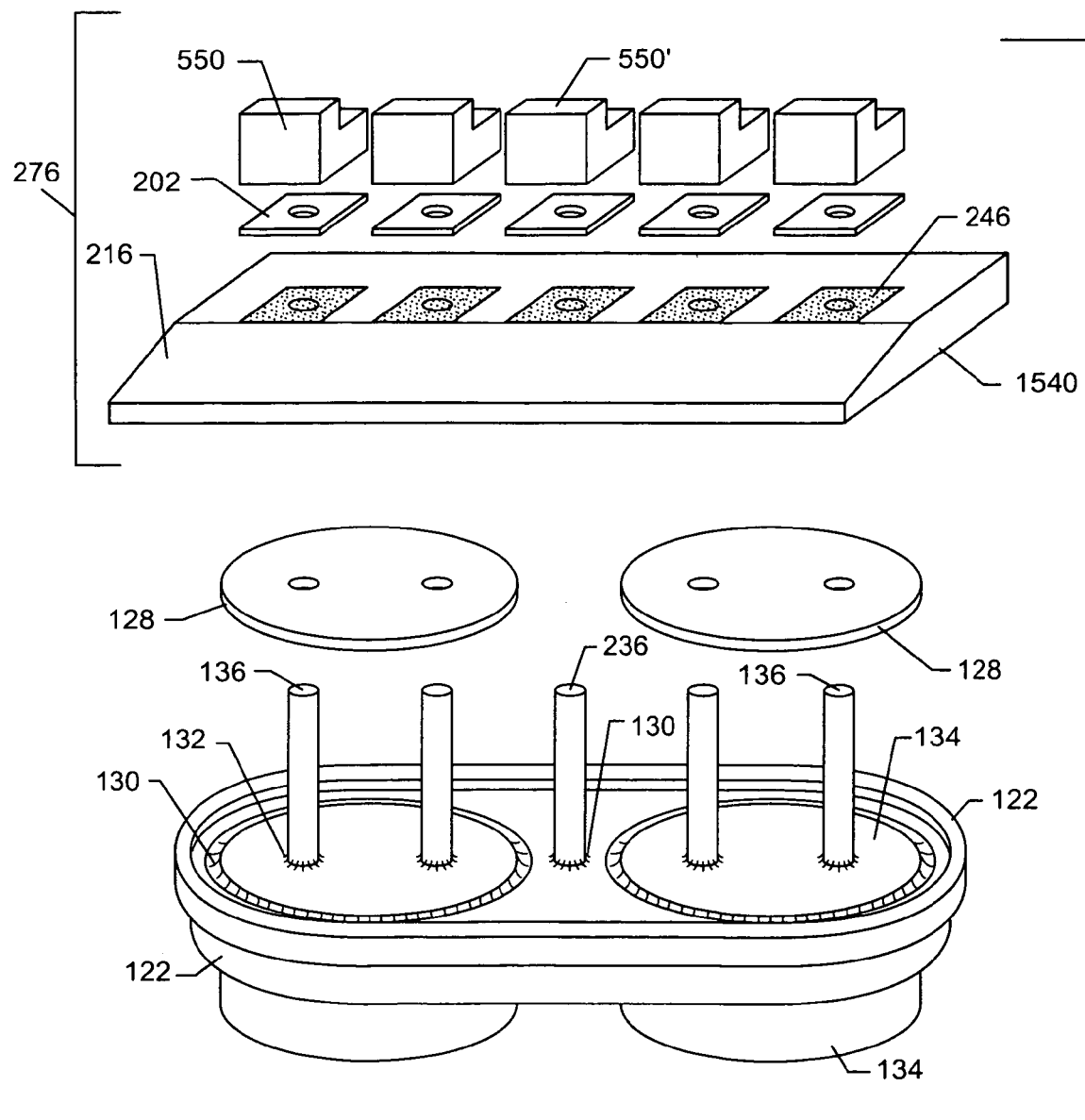
FIG. 40 is an exploded perspective view of a quadpolar feedthrough assembly plus a grounded pin embodying the present invention.

FIG. 40 illustrates an exploded view of an internally grounded quadpolar plus ground pin hermetic terminal for human implant applications. The ground pin 236 is shown welded to ferrule 122 in the center which is desirable.

With continuing reference to FIG. 40, one can see that alumina substrate 1540 of the present invention has rectangular metallized areas 246 for convenient attachment of wire bond pads 550 and 550' to these metallized areas using braze preforms 202. The wire bond pads 550 and 550' would typically be attached to substrate 1540 as a first step by reflowing the braze preforms 202 in a high temperature vacuum brazing furnace. Adhesive coated nonconductive polyimide insulating washer 228 would then be put in place. The pre-assembly 276 consisting of the substrate 1540 with the gold braze wire bond pad 550 would then be slipped in place over the five terminal pins 136. This sandwich, as shown exploded in FIG. 40, is then clamped together and cured at a high temperature such that the nonconductive bonding washer 128 are cured. A laser weld connection is made between each lead wire 136 and each corresponding wire bond pad 550.

Figure 41:
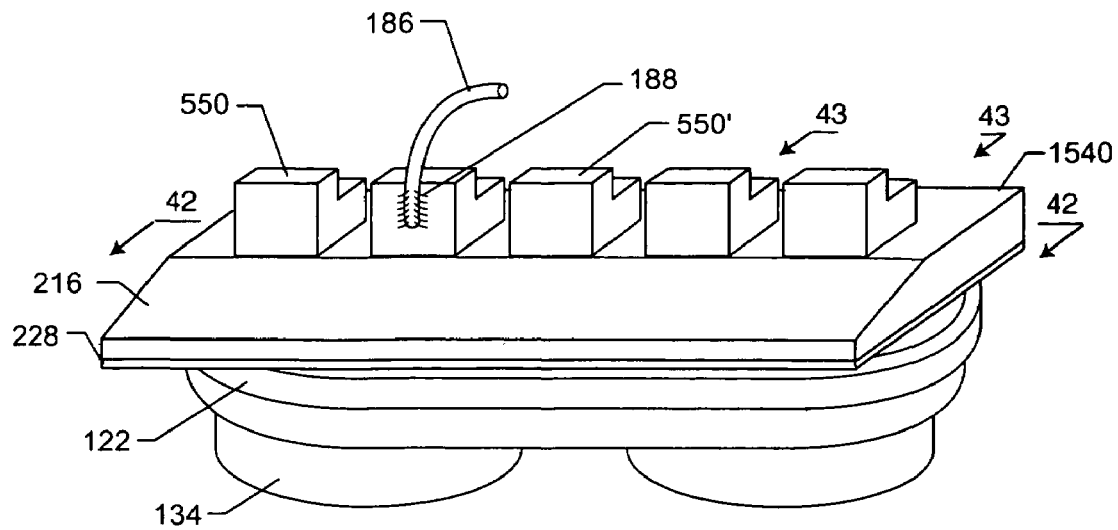
FIG. 41 is a perspective view of the assembled feedthrough terminal assembly of FIG. 40.

FIG. 41 illustrates the completed assembly of FIG. 40. For illustrative purposes a lead wire 186, which would be routed from the internal circuits of an implantable medical device such as a cardiac pacemaker, is shown wire bonded 188 to one of the wire bond pads 550. Wire bonding equipment, including automated systems with robotic controls typically have a rather large feed head through which the wire to be bonded protrudes. The wire bond equipment feed head tapers to a point and is somewhat conical in cross-section. Accordingly, substrate 1540 has been tapered down into area 216 thereby providing sufficient space for the wire bond head to come in and properly engage the leads 186 and wire bond pads 550. This is a novel aspect of the present invention that can be adapted to many other of the substrates that are described in this patent application. The center wire bond pad 550' is grounded to ferrule 122 of the hermetic terminal.

Referring now back to FIG. 40, one can see by observing terminal pin 236 and gold braze or weld 130 that terminal pin 286 is both mechanically and electrically connected to the center of overall metallic ferrule structure 122.

Wire bond pad 550' is not necessary in all implantable medical devices. In certain cardiac pacemakers and implantable defibrillators, a convenient grounding location is an important feature. For example, in an implantable defibrillator cardioverter, where the titanium housing of the device can also be a cardiac shock electrode, a low resistance connection must be made from the high voltage output circuitry of the implantable defibrillator to its overall titanium housing 124. Accordingly, wire bond pad 550' provides a convenient place to make such a connection. The rest of this shock electrode circuit is completed by laser welding the ferrule 122 into the overall housing or titanium shield 124 of the implantable medical device (not shown).

Figure 42:
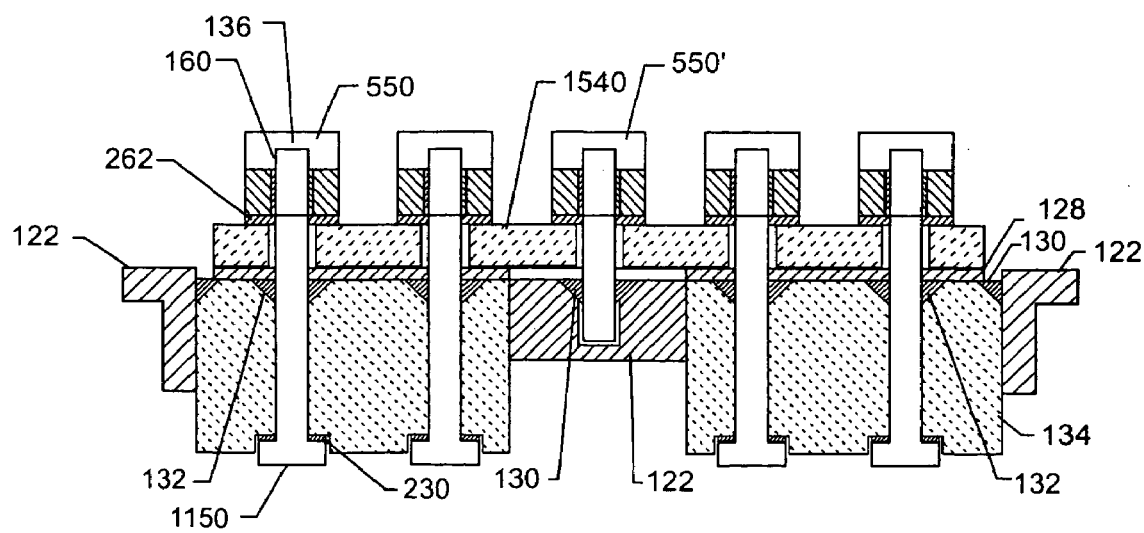
FIG. 42 is a cross-sectional view taken generally along the line 42—42 of FIG. 41.

FIG. 42 illustrates a cross-sectional view of the quadpolar plus ground pin assembly of FIG. 41. Referring to FIG. 42, one can see that the substrate 1540 has been solidly bonded to the alumina insulator 134 of the hermetic terminal using two nonconductive insulating washers 128. Wire bond pads 550 have been attached by brazing material 202 to the top metallization 146 of the alumina substrate 1540.

Wire bond pads 1150 can be placed on the bodyfluid side of the hermetic terminal assembly and are brazed directly to the alumina insulator 134. Human body fluid is very corrosive. Accordingly, the wire bond pads 1150, the braze and the underlying pin material 136 must be of suitable biocompatible material. Such materials include the group of platinum, niobium, gold, tantalum, titanium, stainless and their various alloys including alloys containing iridium and nickel.

Attachment of terminal pin 186 (not shown) to the body fluid side wire bond pads 1150 is preferably done by direct lead wire welding or brazing. These wires 186 would typically connect from the wire bond pads 1150 to the connector or header block (not shown) of a cardiac pacemaker and the like. If attachment to wire bond pads 1150 is by mechanical attachment, ultrasonic bonding or thermosonic bonding, then wire bond pads 1150 would either be of gold or would require an ultra-pure gold over plating.

Figure 43:
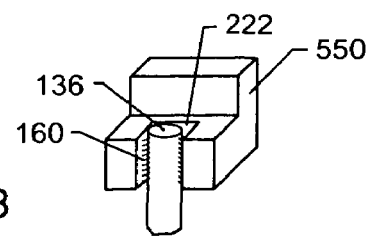
FIG. 43 is a perspective view of modified L-shaped wire bond pad taken generally of the structure illustrated by the line 43—43 in FIG. 41.

FIG. 43 illustrates a rotated close up view of one of the wire bond pads 550 of FIG. 41. As one can see, the laser weld area 160 is relatively long about both sides of the terminal pin 136. This not only makes a highly reliable electrical connection, but is also easy to manufacture. This is because there is a natural fillet area that is formed between the outside diameter of terminal pin 136, and the inside of the slot 222 which has been conveniently machined or stamped into the wire bond pad 550. As previously mentioned, it would be typical that wire bond pad 550 be of Kovar, Alloy 42, or other metallic material. Wire bond pad 550 would typically be first nickel plated and over plated with an ultra pure soft gold.

Figure 44:
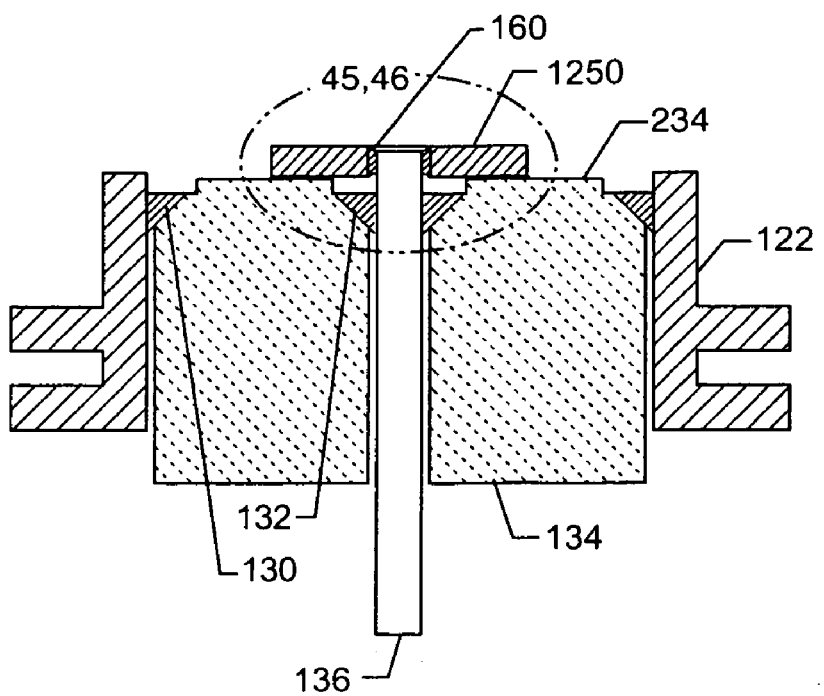
FIG. 44 is a cross-sectional view of another unipolar hermetic terminal embodying the invention.

FIG. 44 illustrates another embodiment of the present invention. Shown is a unipolar hermetic terminal. The novel aspect shown in FIG. 44 is that there are no nonconductive insulating washers that have been described in previous figures. A unique feature is the pedestal area which is the protruding part of the alumina insulator 134 labeled as 234. Alumina ceramic insulators can be machined, made of pressed powders and then fired, or laser cut. Accordingly, formation of the pedestal area 234 is a relatively easy and inexpensive manufacturing operation. As previously described, gold brazes 130 and 132 make a mechanical and hermetic seal connection between alumina insulator 134 and both the ferrule 122 and terminal pin 136. Fixturing applies pressure to center and pushes down on wire bond pad 1250 while automated equipment formed the laser weld 160 as shown.

Again referring to FIGS. 44 and 46, one can see that a disadvantage of the wire bond cap 1250 and 1450 shown is that it has a central through hole where the laser weld connection 160 is made to terminal pin 136. This reduces the top surface contact area of the wire bond pad 1250 that is available for subsequent wire bonding to the terminal pin 136 of the internal circuits of the implantable medical device.

Figure 45:
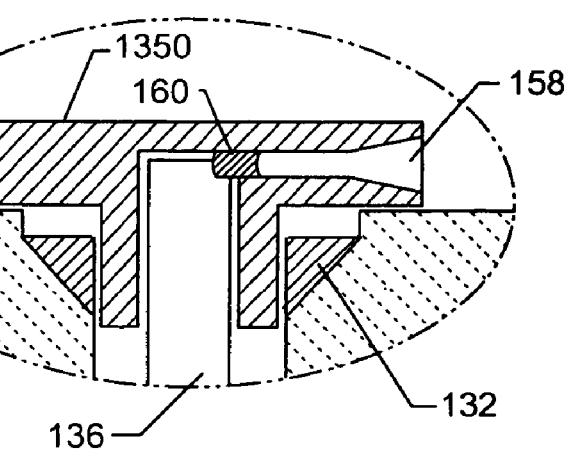
FIG. 45 is an enlarged sectional view of an alternative structure taken along line 45 of FIG. 44.
Figure 46:
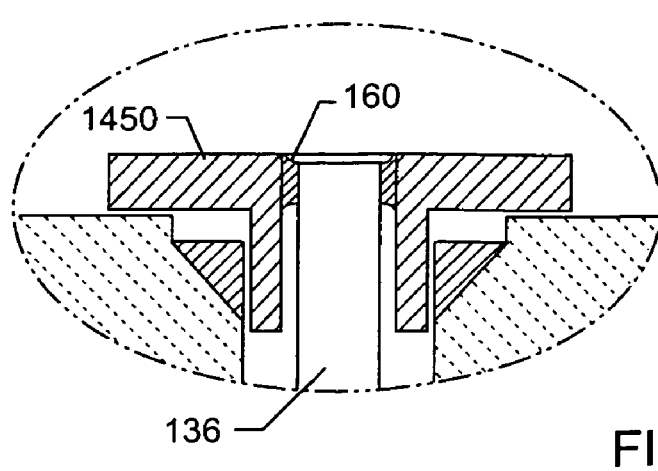
FIG. 46 is an enlarged sectional view of an alternative structure taken along the line 46 in FIG. 44.

In the case where additional surface area would be required, a preferable wire bond pad 1350 is as described in FIG. 45. The wire bond pad 1350 as illustrated in FIG. 45 has a previously described aperture 158 for convenient laser welding 160 of the wire bond cap to terminal pin 136.

Wire bond pads can also be put on the opposite or body fluid side of the hermetic terminal insulator. This can be done by co-bonding the alumina substrate with wire bond pads of the present invention or as mentioned, the alumina insulator itself can be modified to incorporate an embedded wire bond pad or even embedded circuit traces.

Figure 47:
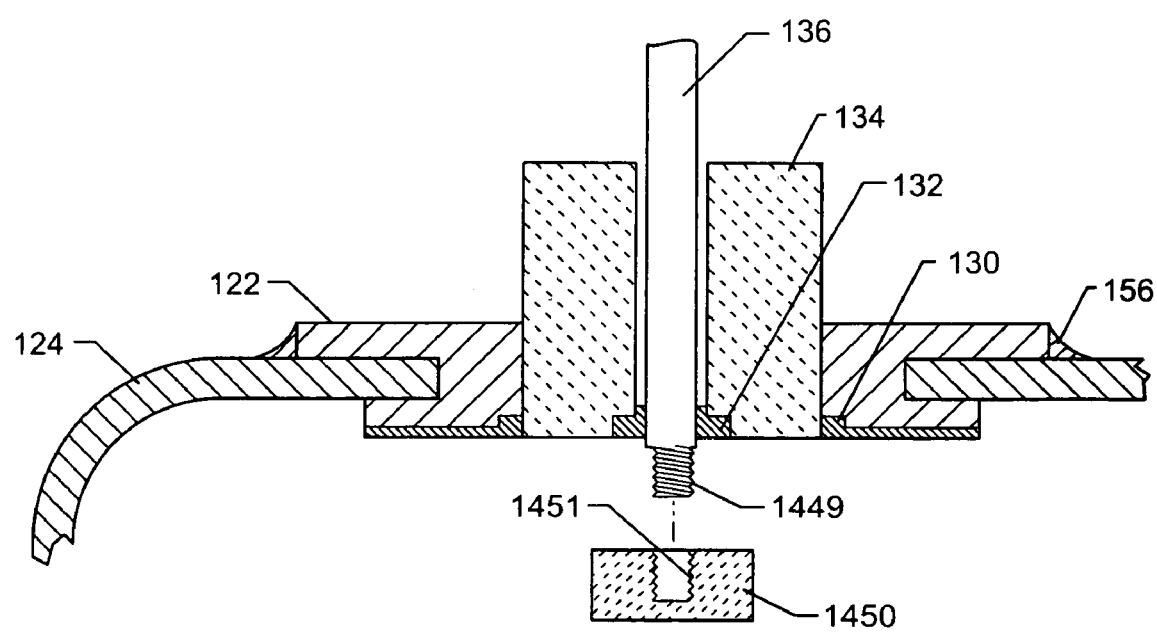
FIG. 47 is a sectional view of yet another embodiment of the invention similar to that shown in FIG. 6, wherein the wire bond cap has been drilled and threaded.

In FIG. 47, an alternative method of attaching wire bond cap 1450 is illustrated. FIG. 47 is similar to FIG. 6. The novel wire bond cap 1450 has been drilled and threaded 1451 as shown. This is designed to mate up with a threaded portion 1449 of terminal pin 136. Such threads can typically be formed using screw machines and the like. The threaded-on wire bond cap 1450 is typically constructed of Kovar or Alloy 42 which is then nickel plated and then over plated with pure gold suitable for wire bonding. The shape of the wire bond cap of 1450 can be circular, rectangular, hexagonal or any other shape to fit a convenient tool for screwing the device into place. Additionally, a bonding washer (not shown) could be used sandwiched between the threaded wire bond cap 1450 and the top surface of the insulator 134. After threading the wire bond cap 1450 into place, this washer could be cured which would firmly seat the threaded cap into position so that it would be able to withstand shock and vibration forces. Of course, there are a number of other methods of securing the threaded portion 1450 and 1499 using resistance welding, laser welding, solders, thermal-setting conductive adhesives on the threads and the like. Additionally, many of the wire bond embodiments shown throughout the Figures in this application could be adapted to threading as illustrated in FIG. 47.

Figure 48:
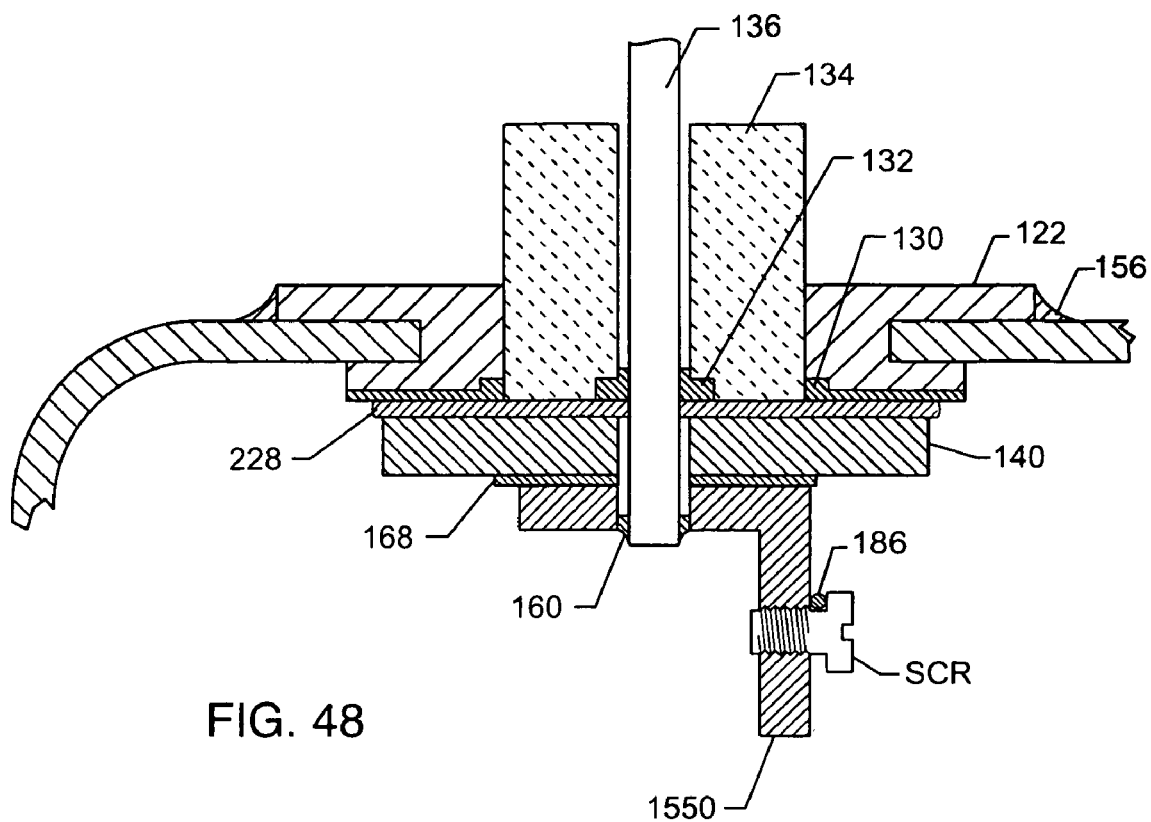
FIG. 48 is a sectional view of yet another embodiment of the invention similar to that illustrated in FIG. 16, wherein the wire bond cap has been modified to include a threaded hole.
Figure 49:
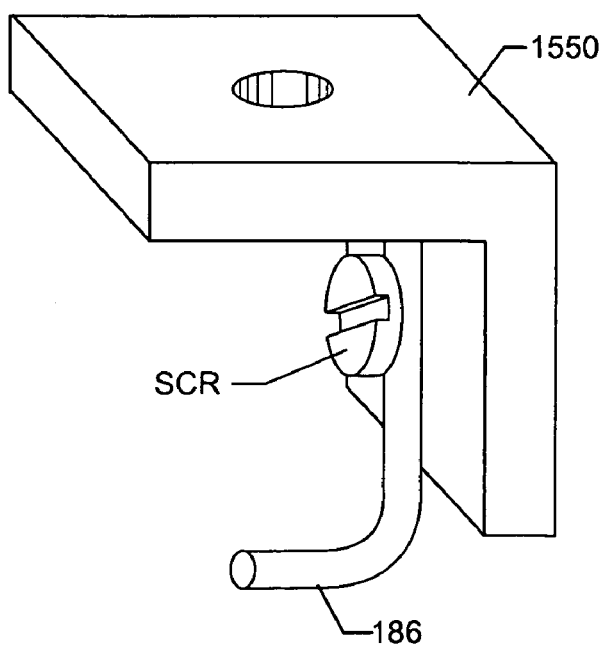
FIG. 49 is an enlarged perspective view of an L-shaped bond pad similar to that shown in FIG. 48, illustrating a screw placed on the opposite side for compressing a wire therebetween.

FIG. 48 is similar to FIG. 16 except that the L-shaped wire bond cap 1550 has been modified to include a threaded hole. This threaded hole is designed to receive a screw or other fastening device shown as SCR. A wire from pacemaker circuitry 186 is shown compressed between the screw SCR and the wire bond cap 1550. In this case, since a mechanical attachment is being made, it is not necessary that the wire bond cap 1550 be of Alloy 42 or Kovar. In fact, wire bond cap 1550 could be from a variety of metals, including something inexpensive like tin-coated copper. The fastener shown as SCR could be a slotted screw, a hex-head screw, an allen-set screw, a rivet, or a variety of other fasteners. FIG. 49 illustrates the screw SCR being placed on the opposite side compressing over wire 186. Such are well known in the art.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. A feedthrough terminal assembly for an active implantable medical device, comprising:
   a conductive ferrule conductively coupled to a housing of the active implantable medical device;
   a conductive terminal pin extending through the ferrule in non-conductive relation;
   an insulator disposed between the terminal pin and the ferrule;
   a structural pad disposed adjacent to the insulator; and
   a lead wire conductively coupled to the terminal pin by means of the structural pad.

2. The assembly of claim 1, wherein the structural pad is mechanically attached to the terminal pin.

3. The assembly of claim 2, wherein the structural pad is threaded onto an end of the terminal pin.

4. The assembly of claim 1, wherein the structural pad comprises a substrate disposed adjacent to a planar surface of the insulator.

5. The assembly of claim 4, wherein the substrate comprises a ceramic-based material.

6. The assembly of claim 4, wherein the substrate is selected from an alumina, ceramic, berrylia, aluminum nitride, Fosterite, polyimide, cyanate ester, barium titanate, epoxy or fiber-reinforced material.

7. The assembly of claim 4, wherein the substrate includes a conductive surface trace having a bonding area.

8. The assembly of claim 7, wherein the lead wire is attached to the bonding area.

9. The assembly of claim 7, including a wire bond pad conductively coupled to the wire bonding area.

10. The assembly of claim 4, wherein the substrate includes a conductive wire bond pad attached thereto, to which the lead wire is conductively coupled.

11. The assembly of claim 10, wherein the wire bond pad includes a first portion conductively coupled to the substrate, and a second portion conductively coupled to the lead wire.

12. The assembly of claim 11, wherein the first and second portions of the wire bond pad are angularly displaced relative to one another.

13. The assembly of claim 4, wherein the substrate includes a recess configured for receiving corresponding conductive wire bond pads therein.

14. The assembly of claim 4, wherein the substrate includes a tapered edge.

15. The assembly of claim 4, wherein the substrate includes an aperture, hold or slot for facilitating laser welding of the substrate to the terminal pin.

16. The assembly of claim 4, including a wire bond pad attached to the substrate through which the terminal pin at least partially extends, the wire bond pad being conductively coupled to the terminal pin, and having an extension to which the lead wire is attached.

17. The assembly of claim 4, wherein the substrate includes multiple apertures therethrough for passage of multiple terminal pins, including a ground pin, and wire bond pads conductively coupled to each terminal pin.

18. The assembly of claim 17, wherein the wire bond pads each include an aperture for receiving a respective terminal pin therethrough, each respective terminal pin and wire bond pad being conductively attached to one another.

19. The assembly of claim 18, wherein the terminal pins and the wire bond pads are welded to one another.

20. The assembly of claim 1, wherein the structural pad comprises a substrate having an aperture into which the terminal pin extends.

21. The assembly of claim 20, wherein the substrate aperture is substantially lined with conductive material to define an electrical path from the terminal pin to the lead wire.

22. The assembly of claim 21, including a conductive insert disposed within a substrate recess for conductively coupling the substrate with the terminal pin.

23. The assembly of claim 22, wherein the insert comprises a conductive insert ring disposed within the recess in the substrate, the insert ring being conductively coupled to the terminal pin and the substrate.

24. The assembly of claim 23, wherein the substrate includes a conductive trace conductively coupled to the insert ring, and defining a lead wire bonding area on a surface of the substrate.

25. The assembly of claim 24, including a wire bond pad conductively coupled to the bonding area.

26. The assembly of claim 20, wherein a portion of the terminal pin extending from the substrate is bent, and the wire bond pad is configured for placement over the bent portion of the terminal pin.

27. The assembly of claim 1, wherein the structural pad comprises a conductive wire bond pad conductively coupled to the terminal pin.

28. The assembly of claim 27, wherein the wire bond pad is comprised of Kovar or Alloy 42.

29. The assembly of claim 27, wherein the end of the terminal pin and the wire bond pad are conductively attached to one another.

30. The assembly of claim 29, wherein the wire bond pad includes a socket for receiving an end of the terminal pin therein.

31. The assembly of claim 30, wherein the socket comprises an aperture, hole or slot extending at least partially through the wire bond pad.

32. The assembly of claim 29, wherein the wire bond pad is laser welded to the terminal pin.

33. The assembly of claim 32, Wherein the wire bond pad includes a through-hole or slot to facilitate laser melting of a tip of the terminal pin.

34. The assembly of claim 29, wherein the wire bond pad is disposed over an end of the terminal pin.

35. The assembly of claim 27, wherein the wire bond pad includes an aperture through which the terminal pin extends.

36. The assembly of claim 27, wherein the wire bond pad includes an extension to which the lead wire is attached.

37. The assembly of claim 27, wherein the lead wire is mechanically attached to the wire bond pad.

38. The assembly of claim 37, including a screw to mechanically attach the lead wire to the wire bond pad.

39. The assembly of claim 1, wherein the structural pad includes embedded conductive circuit traces extending from the terminal pin to a conductive wire bonding area on a surface of the structural pad.

40. The assembly of claim 1, wherein the structural pad comprises a rectilinear multilayer substrate.

41. A feedthrough terminal assembly for an active implantable medical device, comprising:
 a conductive ferrule conductively coupled to a housing of the active implantable medical device;
 a conductive terminal pin extending through the ferrule in non-conductive relation;
 an insulator disposed between the terminal pin and the ferrule;
 a wire bond pad conductively coupled to the terminal pin; and
 a lead wire conductively coupled to the wire bond pad.

42. The assembly of claim 41, wherein the wire bond pad includes a socket for receiving an end of the terminal pin therein.

43. The assembly of claim 42, wherein the socket comprises an aperture, hole or slot extending at least partially through the wire bond pad.

44. The assembly of claim 41, wherein the wire bond pad is mechanically attached to the terminal pin.

45. The assembly of claim 44, wherein the structural pad is threaded onto an end of the terminal pin.

46. The assembly of claim 41, wherein the wire bond pad includes first and second portions, the lead wire being attached to the second portion.

47. The assembly of claim 46, wherein the first and second portions of the wire bond pad are angularly displaced relative to one another.

48. The assembly of claim 41, wherein a portion of the terminal pin extending from the insulator is bent, and the wire bond pad is configured for placement over the bent portion of the terminal pin.

49. The assembly of claim 41, wherein the wire bond pad is comprised of Kovar or Alloy 42.

50. The assembly of claim 41, wherein the end of the terminal pin and the wire bond pad are conductively attached to one another.

51. The assembly of claim 50, wherein the wire bond pad is laser welded to the terminal pin.

52. The assembly of claim 51, wherein the wire bond pad includes a through-hole or slot to facilitate laser melting of a tip of the terminal pin.

53. The assembly of claim 41, wherein the wire bond pad is disposed over an end of the terminal pin.

54. The assembly of claim 41, wherein the wire bond pad includes an aperture through which the terminal pin extends.

55. The assembly of claim 41, wherein the wire bond pad includes an extension to which the lead wire is attached.

56. The assembly of claim 41, wherein the lead wire is mechanically attached to the wire bond pad.

57. The assembly of claim 56, including a screw to mechanically attach the lead wire to the wire bond pad.

58. A feedthrough terminal assembly for an active implantable medical device, comprising:
 a conductive ferrule conductively coupled to a housing of the active implantable medical device;
 a conductive terminal pin extending through the ferrule in non-conductive relation;
 an insulator disposed between the terminal pin and the ferrule;
 a substrate disposed adjacent to the insulator and including a conductive circuit or surface trace conductively coupled to the terminal pin; and
 a lead wire conductively coupled to the terminal pin by means of the conductive trace.

59. The assembly of claim 58, wherein the substrate is selected from an alumina, ceramic, berrylia, aluminum nitride, Fosterite, polyimide, cyanate ester, barium titanate, epoxy or fiber-reinforced material.

60. The assembly of claim 58, wherein the substrate includes a conductive surface trace having a bonding area for bonding the lead wire or a wire bond pad.

61. The assembly of claim 60, wherein a wire bond pad is attached to the conductive surface trace bonding are, and wherein the lead wire is conductively coupled to the wire bond pad.

62. The assembly of claim 61, wherein the wire bond pad includes a first portion conductively coupled to the substrate conductive surface trace, and a second portion conductively coupled to the lead wire.

63. The assembly of claim 62, wherein the first and second portions of the wire bond pad are angularly displaced relative to one another.

64. The assembly of claim 61, wherein the wire bond pad is comprised of Kovar or Alloy 42.

65. The assembly of claim 61, wherein the wire bond pad includes an extension to which the lead wire is attached.

66. The assembly of claim 61, wherein the lead wire is mechanically attached to the wire bond pad.

67. The assembly of claim 66, including a screw to mechanically attach the lead wire to the wire bond pad.

68. The assembly of claim 58, wherein the substrate includes an aperture into which the terminal pin extends.

69. The assembly of claim 68, wherein the substrate aperture is substantially lined with conductive material to define an electrical path from the terminal pin to the lead wire.

70. The assembly of claim 69, including a conductive insert disposed within a substrate recess for conductively coupling the substrate with the terminal pin.

71. The assembly of claim 70, wherein the insert comprises a conductive insert ring disposed within the recess in the substrate, the insert ring being conductively coupled to the terminal pin and the substrate.

72. The assembly of claim 71, wherein the conductive trace is conductively coupled to the insert ring, and defines a lead wire or wire bond pad bonding area on a surface of the substrate.

73. The assembly of claim 58, wherein the substrate includes a tapered edge.

74. The assembly of claim 58, wherein the substrate includes an aperture, hold or slot for facilitating laser welding of the substrate to the terminal pin.

75. The assembly of claim 58, wherein the substrate includes multiple apertures therethrough for passage of multiple terminal pins, including a ground pin, and wire bond-pads conductively coupled to each terminal pin.

76. The assembly of claim 58, wherein the structural pad includes embedded conductive circuit traces extending from the terminal pin to a conductive wire bonding area on a surface of the structural pad.

77. The assembly of claim 58, wherein the structural pad comprises a rectilinear multilayer substrate.

78. A feedthrough terminal assembly for an active implantable medical device, comprising:
   a conductive ferrule conductively coupled to a housing of the active implantable medical device;
   a conductive terminal pin extending through the ferrule in non-conductive relation;
   an insulator disposed between the terminal pin and the ferrule;
   a substrate disposed adjacent to the insulator;
   a wire bond pad attached to the substrate so as to be conductively coupled to the terminal pin; and
   a lead wire conductively coupled to the terminal pin by means of the wire bond pad.

79. The assembly of claim 78, wherein the substrate is selected from an alumina, ceramic, berrylia, aluminum nitride, Fosterite, polyimide, cyanate ester, barium titanate, epoxy or fiber-reinforced material.

80. The assembly of claim 78, wherein the substrate includes a conductive surface trace having a bonding area to which the wire bond pad is attached.

81. The assembly of claim 78, wherein the wire bond pad includes a first portion conductively coupled to the substrate, and a second portion conductively coupled to the lead wire.

82. The assembly of claim 81, wherein the first and second portions of the wire bond pad are angularly displaced relative to one another.

83. The assembly of claim 78, wherein the substrate includes an aperture into which the terminal pin extends.

84. The assembly of claim 83, wherein the substrate aperture is substantially lined with conductive material to define an electrical path from the terminal pin to the wire bond pad and the lead wire.

85. The assembly of claim 78, including a conductive insert disposed within a substrate recess for conductively coupling the substrate with the terminal pin.

86. The assembly of claim 85, wherein the insert comprises a conductive insert ring disposed within the recess in the substrate, the insert ring being conductively coupled to the terminal pin and the substrate.

87. The assembly of claim 86, wherein the substrate includes a conductive trace conductively coupled to the insert ring, and defining a lead wire bonding area on a surface of the substrate.

88. The assembly of claim 87, wherein the wire bond pad is conductively coupled to the bonding area.

89. The assembly of claim 78, wherein the substrate includes a recess configured for receiving a corresponding conductive wire bond pad therein.

90. The assembly of claim 78, wherein a portion of the terminal pin extending from the substrate is bent, and the wire bond pad is configured for placement over the bent portion of the terminal pin.

91. The assembly of claim 78, wherein the substrate includes a tapered edge.

92. The assembly of claim 78, wherein the wire bond pad is comprised of Kovar or Alloy 42.

93. The assembly of claim 78, wherein the wire bond pad includes a socket for receiving an end of the terminal pin therein.

94. The assembly of claim 93, wherein the socket comprises an aperture, hole or slot extending at least partially through the wire bond pad.

95. The assembly of claim 94, wherein the wire bond pad is laser welded to the terminal pin.

96. The assembly of claim 94, wherein the wire bond pad includes an aperture through which the terminal pin extends.

97. The assembly of claim 78, wherein the wire bond pad includes an extension to which the lead wire is attached.

98. The assembly of claim 78, wherein the substrate includes an aperture, hold or slot for facilitating laser welding of the substrate to the terminal pin.

99. The assembly of claim 78, wherein the lead wire is mechanically attached to the wire bond pad.

100. The assembly of claim 99, including a screw to mechanically attach the lead wire to the wire bond pad.

101. The assembly of claim 78, including a wire bond pad attached to the substrate through which the terminal pin at least partially extends, the wire bond pad being conductively coupled to the terminal pin, and having an extension to which the lead wire is attached.

102. The assembly of claim 78, wherein the substrate includes multiple apertures therethrough for passage of multiple terminal pins, including a ground pin, and wire bond pads conductively coupled to each terminal pin.

103. The assembly of claim 102, wherein the wire bond pads each include an aperture for receiving a respective terminal pin therethrough, each respective terminal pin and wire bond pad being conductively attached to one another.

104. The assembly of claim 103, wherein the terminal pins and the wire bond pads are welded to one another.

105. The assembly of claim 78, wherein the structural pad includes embedded conductive circuit traces extending from the terminal pin to a conductive wire bonding area on a surface of the structural pad.

106. The assembly of claim 78, wherein the structural pad comprises a rectilinear multilayer substrate.

* * * * *